(12) United States Patent
Rohde et al.

(10) Patent No.: US 7,892,772 B2
(45) Date of Patent: Feb. 22, 2011

(54) TARGETED UBIQUITINATION OF PROTEINS AND SCREENING METHODS USING A NEW CLASS OF UBIQUITIN LIGASE PROTEINS

(75) Inventors: John Roy Rohde, Paris (FR); Claude Rene Raoul Parsot, Paris (FR); Philippe Joseph Sansonetti, Paris (FR)

(73) Assignee: ITI Scotland Limited, Scotland (GB)

( * ) Notice: Subject to any disclaimer, the term of this patent is extended or adjusted under 35 U.S.C. 154(b) by 461 days.

(21) Appl. No.: 11/685,122

(22) Filed: Mar. 12, 2007

(65) Prior Publication Data

US 2008/0261241 A1 Oct. 23, 2008

(51) Int. Cl.
*C12P 21/04* (2006.01)
*C12N 15/11* (2006.01)

(52) U.S. Cl. ............... 435/7.8; 435/183; 435/255.1; 435/325; 435/320.1; 435/69.1

(58) Field of Classification Search .................. None
See application file for complete search history.

(56) References Cited

U.S. PATENT DOCUMENTS

| | | | | |
|---|---|---|---|---|
| 6,136,542 | A * | 10/2000 | Demers et al. ............... 435/6 |
| 6,737,244 | B2 * | 5/2004 | Issakani et al. ............ 435/7.92 |
| 6,740,495 | B1 * | 5/2004 | Issakani et al. ............ 435/7.92 |
| 2002/0042083 | A1 * | 4/2002 | Issakani et al. .............. 435/7.9 |
| 2003/0204868 | A1 * | 10/2003 | Collmer et al. ............. 800/279 |
| 2006/0035230 | A1 * | 2/2006 | Martin et al. ................. 435/6 |
| 2007/0162994 | A1 * | 7/2007 | Collmer et al. ............. 800/278 |

OTHER PUBLICATIONS

Okuda, Jun et al, Biochemical and Biophysical Research Communications, vol. 333, 2005, pp. 531-539, Shigella effector IpaH9.8 binds to a splicing factor U2AF to modulate host immune responses.*
Haraga, A et al, Infection and Immunity, Jul. 2003, pp. 4052-4058, vol. 71(7), A *Salmonella enterica* Serovar Typhimurium translocated Leucine-Rich Repeat Effector protein inhibits NF-kB dependent Gene Expression.*
Munro, P et al, Current Opinion in Microbiology, vol. 10(1), Feb. 2007, pp. 39-46, Bacteria and the ubiquitin pathway.*
Janjusevic, Radmila e tal, Science vol. 311, Jan. 13, 2006, pp. 222-226, A Bacterial inhibitor of Host Programed Cell Death Defenses Is an E3 Ubiquitin Ligase.*

(Continued)

*Primary Examiner*—Mark Navarro
*Assistant Examiner*—Ginny Portner
(74) *Attorney, Agent, or Firm*—Oblon, Spivak, McClelland, Maier & Neustadt, L.L.P.

(57) ABSTRACT

Members of the IpaH superfamily constitute a novel class of E3 ubiquitin ligases which are useful for engineering products which modulate trafficking and destruction of target proteins inside a cell and useful targets for identifying new antimicrobial molecules which modulate, especially inhibit, E3 ligases.

4 Claims, 7 Drawing Sheets

OTHER PUBLICATIONS

Abramovitch, Robert B et al, PNAS, Feb. 21, 2006, vol. 103(8), pp. 2851-2856, Type III effector AvrPtoB requires intrinsic E3 ubiuitin ligase activity to suppress plant cell death and immunity.*

Zhang, Y et al, Molecular Microbiology, vol. 62(3), pp. 786-793, first published online Sep. 21, 2006, Dec. 2006 issue, The inflammation-associated Salmonella SopA is a Hect-like E3 ubiquitin ligase.*

Swiss-Prot Accession No. Q4ZMD6, Jun. 2005, Pseudomonas syringae AvrPtoB protein.*

Swiss-Prot Accession No. Q8ZNR3, Mar. 2002, Salmonella SopA protein.*

* cited by examiner

FIG. 4-A

Amino Acid Sequence of IpaH 9.8 from *Shigella Flexneri*

```
Met Leu Pro Ile Asn Asn Asn Phe Ser Leu Pro Gln Asn Ser Phe Tyr
1               5                   10                  15

Asn Thr Ile Ser Gly Thr Tyr Ala Asp Tyr Phe Ser Ala Trp Asp Lys
                20                  25                  30

Trp Glu Lys Gln Ala Leu Pro Gly Glu Glu Arg Asp Glu Ala Val Ser
            35                  40                  45

Arg Leu Lys Glu Cys Leu Ile Asn Asn Ser Asp Glu Leu Arg Leu Asp
    50                  55                  60

Arg Leu Asn Leu Ser Ser Leu Pro Asp Asn Leu Pro Ala Gln Ile Thr
65                  70                  75                  80

Leu Leu Asn Val Ser Tyr Asn Gln Leu Thr Asn Leu Pro Glu Leu Pro
                85                  90                  95

Val Thr Leu Lys Lys Leu Tyr Ser Ala Ser Asn Lys Leu Ser Glu Leu
            100                 105                 110

Pro Val Leu Pro Pro Ala Leu Glu Ser Leu Gln Val Gln His Asn Glu
        115                 120                 125

Leu Glu Asn Leu Pro Ala Leu Pro Asp Ser Leu Leu Thr Met Asn Ile
    130                 135                 140

Ser Tyr Asn Glu Ile Val Ser Leu Pro Ser Leu Pro Gln Ala Leu Lys
145                 150                 155                 160

Asn Leu Arg Ala Thr Arg Asn Phe Leu Thr Glu Leu Pro Ala Phe Ser
                165                 170                 175

Glu Gly Asn Asn Pro Val Val Arg Glu Tyr Phe Phe Asp Arg Asn Gln
            180                 185                 190

Ile Ser His Ile Pro Glu Ser Ile Leu Asn Leu Arg Asn Glu Cys Ser
        195                 200                 205

Ile His Ile Ser Asp Asn Pro Leu Ser Ser His Ala Leu Gln Ala Leu
    210                 215                 220

Gln Arg Leu Thr Ser Ser Pro Asp Tyr His Gly Pro Arg Ile Tyr Phe
225                 230                 235                 240
```

FIG. 4-B

Ser Met Ser Asp Gly Gln Gln Asn Thr Leu His Arg Pro Leu Ala Asp
            245                 250                 255

Ala Val Thr Ala Trp Phe Pro Glu Asn Lys Gln Ser Asp Val Ser Gln
            260                 265                 270

Ile Trp His Ala Phe Glu His Glu His Ala Asn Thr Phe Ser Ala
        275                 280                 285

Phe Leu Asp Arg Leu Ser Asp Thr Val Ser Ala Arg Asn Thr Ser Gly
        290                 295                 300

Phe Arg Glu Gln Val Ala Ala Trp Leu Glu Lys Leu Ser Ala Ser Ala
305                 310                 315                 320

Glu Leu Arg Gln Gln Ser Phe Ala Val Ala Ala Asp Ala Thr Glu Ser
            325                 330                 335

Cys Glu Asp Arg Val Ala Leu Thr Trp Asn Asn Leu Arg Lys Thr Leu
            340                 345                 350

Leu Val His Gln Ala Ser Glu Gly Leu Phe Asp Asn Asp Thr Gly Ala
            355                 360                 365

Leu Leu Ser Leu Gly Arg Glu Met Phe Arg Leu Glu Ile Leu Glu Asp
        370                 375                 380

Ile Ala Arg Asp Lys Val Arg Thr Leu His Phe Val Asp Glu Ile Glu
385                 390                 395                 400

Val Tyr Leu Ala Phe Gln Thr Met Leu Ala Glu Lys Leu Gln Leu Ser
            405                 410                 415

Thr Ala Val Lys Glu Met Arg Phe Tyr Gly Val Ser Gly Val Thr Ala
            420                 425                 430

Asn Asp Leu Arg Thr Ala Glu Ala Met Val Arg Ser Arg Glu Glu Asn
        435                 440                 445

Glu Phe Thr Asp Trp Phe Ser Leu Trp Gly Pro Trp His Ala Val Leu
        450                 455                 460

Lys Arg Thr Glu Ala Asp Arg Trp Ala Gln Ala Glu Glu Gln Lys Tyr
465                 470                 475                 480

FIG. 4C

```
Glu Met Leu Glu Asn Glu Tyr Pro Gln Arg Val Ala Asp Arg Leu Lys
                485                 490                 495

Ala Ser Gly Leu Ser Gly Asp Ala Asp Ala Glu Arg Glu Ala Gly Ala
            500                 505                 510

Gln Val Met Arg Glu Thr Glu Gln Gln Ile Tyr Arg Gln Leu Thr Asp
        515                 520                 525

Glu Val Leu Ala Leu Arg Leu Ser Glu Asn Gly Ser Gln Leu His His
    530                 535                 540

Ser
545
```

TARGETED UBIQUITINATION OF PROTEINS AND SCREENING METHODS USING A NEW CLASS OF UBIQUITIN LIGASE PROTEINS

BACKGROUND OF THE INVENTION

1. Field of the Invention

Polypeptides in the IpaH superfamily have been discovered to be a new class of E3 ubiquitin ligases unrelated to known E3 ubiquitin ligases such as RING, U box, and HECT-domain ligases. A ubiquitin ligase attaches the protein ubiquitin to a substrate protein. This post-translation modification affects the intracellular trafficking of the ubiquitinated substrate protein and has been shown to direct a ubiquitinated substrate protein to the proteasome for destruction. The ligase of the invention may be used to construct polypeptides which recognize a specific substrate protein and ubiquitinate it or to identify molecules which block or inhibit E3 ubiquitin ligase activity of the IpaH superfamily, such as E3 ligases expressed by the bacterial pathogens *Salmonella* and *Shigella*.

2. Description of the Related Art

The specific and covalent addition of ubiquitin to proteins, known as ubiquitination, is a eukaryotic-specific modification central to many cellular processes, such as cell cycle progression, transcriptional regulation, and hormone signaling. Ubiquitination involves the conjugation of one or more ubiquitin moieties on to a substrate or target protein. Mono- and multi-ubiquitinations can trigger an alteration of the localization and/or activity of a target protein, while poly-ubiquitination can modulate the properties of the target protein or constitute a signal for its degradation by the 26s proteasome, Angot et al., PLOS Pathogens 3:0001 (January, 2007).

The regulated destruction of proteins via the ubiquitin proteasome pathway governs many cellular processes including cell-cycle progression and signal transduction pathways, such as the NF-κB pathway. Invading pathogens are sensed by host cells through surveillance systems that initiate signalling cascades alerting the immune system to the presence of pathogens. These signalling cascades include both MAPK and nuclear factor-κB (NF-κB) programs that induce cytokine production and ultimately result in inflammation (Inohara et al., 2005).

The process of ubiquitination requires a ubiquitin-activating enzyme (E1) which uses ATP to activate the ubiquitin protein, a limited number of ubiquitin-conjugating enzymes (E2) which receive the activated ubiquitin and can transfer an activated ubiquitin molecule to an ubuitin ligase or to a substrate protein in the presence of an ubiquitin ligase, and a large number of ubiquitin-ligase enzymes (E3) which recognize and recruit particular substrate proteins and thus control the nature and the specificity of ubiquitination.

The C-terminal Gly residue of ubiquitin is charged via a thioester linkage onto a Cys residue of E1 and transferred to a Cys residue of E2s. E3s recruit ubiquitinated E2s to specific substrates that are ubiquitinated on Lys residues by an amide linkage. RING and U-box E3s promote the transfer of ubiquitin from E2s to targets, whereas HECT-domain E3s transfer ubiquitin onto one of their Cys residues and then to targets (Ardley and Robinson, 2005; Liu, 2004).

The ubiquitin moiety of ubiquitinated targets can then be ubiquitinated on Lys residues 48 or 63 to produce polyubiquitinated targets. Ubiquitin chains constructed by Lys-48 linkages target proteins for destruction by the proteasome whereas those constructed by Lys-63 linkages leads to altered protein function, such as the activation of kinases (Liu, 2004), or localization.

Bacteria of *Shigella* spp. cause shigellosis in humans by invading the colonic mucosa. Their virulence is dependent upon a 200-kb plasmid encoding a type III secretion (T3S) system (Parsot, 2005). The type III secretion (T3S) apparatus involves the injection of bacterial effector proteins into eukaryotic host cells by many gram-negative bacteria pathogenic for plants or animals, (Galan and Cossart, 2005). *Shigella* effector proteins that promote bacterial entry are produced and stored within the bacterium at 37° C. and transit through the T3S apparatus upon contact with epithelial cells (Menard et al., 1994). A second wave of effectors, whose functions are unknown, are produced only after contact with host cells (Demers et al., 1998). These latter effectors include nine closely related IpaH proteins that are the effectors most abundantly produced by *Shigella* (Demers et al., 1998). Expression of these effectors is dependent upon an AraC family member, MxiE, which activates transcription in response to the activation of the T3S apparatus (Mavris et al., 2002; Penno et al., 2005).

Defining the activity of T3S effectors is key to understanding pathogenesis, however, many effectors share little sequence similarity with proteins of known function. T3S effectors are injected into eukaryotic cells and their molecular targets are intracellular. Since yeast have many proteins and processes well conserved in higher eukaryotes, they have been used to model and gain clues as to the roles of effector proteins, such as T3S effectors (Valdivia, 2004).

Recently, studies in yeast helped to elucidate the function of the *Shigella* effectors IpgB1 and IpgB2 that act as G protein mimics (Alto et al., 2006). To gain insight to IpaH activity, the inventors utilized *Saccharomyces cerevisiae* as a surrogate model. It was found that expression of the effector molecule IpaH9.8 in yeast disrupts signalling through the pheromone response MAPK pathway by promoting the proteasome-dependent degradation of the MAPKK Ste7. In vitro assays were used to demonstrate that effectors of the IpaH superfamily, including IpaH9.8 from *Shigella* and SspH1 from *Salmonella*, constitute a novel class of E3 ubiquitin ligases.

BRIEF SUMMARY OF THE INVENTION

One aspect of the invention is a chimeric polynucleotide which encodes a polypeptide construct comprising an E3 ligase catalytic domain from a member of the IpaH superfamily and a recognition domain recognizing a particular substrate, or target, protein.

The term "recognition domain" refers to an amino acid sequence that recognizes or binds to a substrate or target protein. For example, the N-terminal domains, which contain the leucine rich repeat (LRRs) region of IpaH9.8 from *Shigella flexneri* and SspH1 from *Salmonella enterica*, are examples of recognition domains for the yeast protein Ste7 and the mammalian protein PKN1, respectively.

The term "construct" includes fusion protein constructs, for example, those expressed by recombinant DNA encoding a C-terminal segment of an Ipah-superfamily E3 ligase and encoding an exogenous an N-terminal recognition domain. Constructs also include chimeric or hybrid proteins produced by means other than gene fusion, e.g., by chemical synthesis or by chemical conjugation of the ligase and recognition domains.

An "exogenous" sequence is a sequence not naturally associated with a given sequence. For example, an exogenous (non-Shigella flexneri IpaH9.8) recognition domain may be fused to the C-terminal domain of IpaH9.8 from *Shigella flexerni* to produce a fusion protein containing a recognition domain exogenous to the IpaH9.8 protein of *Shigella flexerni*.

The chimeric polynucleotide of the invention encodes an active site of the IpaH E3 ligase catalytic domain which includes the sequence Cys-(Xaa)$_n$-Asp (SEQ ID NO: 1), wherein "n" represent at least one up to 20 amino acids or the motif:

(SEQ ID NO: 2)
Trp-Xaa(59,72)-Cys-Xaa-Asp-Xaa(29,31)-Leu-Xaa(8)-

Arg-Xaa(7)-Ala-Xaa(13,22)-Leu-Xaa(9)-Leu-Xaa-Leu.

(SEQ ID NO: 2)
Trp-Xaa(59,72)-Cys-Xaa-Asp-Xaa(29,31)-Leu-Xaa(8)-

Arg-Xaa(7)-Ala-Xaa(13,22)-Leu-Xaa(9)-Leu-Xaa-Leu.

This motif is shared by IpaH9.8 from *Shigella* and SspH1 from *Salmonella*. For example, the motif emboldened in the sequence depicted below is from IpaH9.8 of *Shigella flexneri* (SEQ ID NO: 4);

```
  1 mlpinnnfsl pqnsfyntis gtyadyfsaw dkwekqalpg eerdeavsrl keclinnsde 61 lrldrlnlss lpdnlpaqit llnvsynqlt nlpelpvtlk klysasnkls elpvlppale 121 slqvqhnele nlpalpdsll tmnisyneiv slpslpqalk nlratrnflt elpafsegnn 181 pvvreyffdr nqishipesi lnlrnecsih isdnplssha lqalqrltss pdyhgpriyf 241 smsdgqqntl hrpladavta wfpenkqsdv sqiwhafehe ehantfsafl drlsdtvsar 301 ntsgfreqva awleklsasa elrqqsfava adatescedr valtwnnlrk tllvhqaseg 361 lfdndtgall slgremfrle ilediardkv rtlhfvdeie vylafqtmla eklqlstavk 421 emrfygvsgv tandlrtaea mvrsreenef tdwfslwgpw havlkrtead rwalaeeqky 481 emleneypqr vadrlkasgl sgdadaerea gaqvmreteq qiyrqltdev lalrlpengs 541 qlhhs
```

The catalytic domain may also obtained from a gene encoding IpaH9.8 from *Shigella flexneri* (SEQ ID NO: 3) or the gene encoding SspH1 of *Salmonella enterica* (SEQ ID NO: 7) or any other gene encoding a member of the IpaH superfamily. The term "catalytic domain" refers to an amino acid sequence that will ligate ubiquitin to a substrate protein. While its catalytic activity in this respect is similar to that of E3 ubiquitin ligases containing an HECT domain, it will have little or no sequence similarity with HECT E3 ligases. The C-terminal domains of IpaH9.8 from *Shigella flexneri* and SspH1 from *Salmonella enterica* are examples of catalytic domains.

The IpaH C-terminal domain shares 25-40% identity with two groups of bacterial proteins that contain a T3S system. Examples of IpaH superfamily members include IpaH9.8 from *Shigella flexneri* and SspH1 from *Salmonella enterica*. Comparisons of other members of this family are provided by FIG. 4 which depicts the alignment of the C-terminal domains of different IpaH superfamily members. IpaH9.8 is a virulence factor expressed by *Shigella* which facilitates colonization of host epithelial cells by its affect on host inflammatory responses. Deletion of the gene encoding IpaH9.8 reduced the ability of *Shigella* to colonize host cells by a factor of thirty, Okuda et al., *Biochem Biophys Res Commun.* 333(2): 531. SspH1 is a *Salmonella enterica* serovar Typhimurium Type III secretion system effector that localizes to the mammalian nucleus and down-modulates production of proinflammatory cytokines by inhibiting nuclear factor (NF)-κB-dependent gene expression, Haraga et al., *Cell Microbiol.* 8(5):837.

"IpaH superfamily" refers to a class of bacterial polypeptides containing a conserved C-terminal domain which is characterized by a shared nine amino acid motif:

"IpaH family" is a group of proteins expressed by *Shigella* which have substantial homology at the C-terminal; and leucine-rich repeats on the N-terminal end.

Variants of an IpaH superfamily catalytic domain or of a recognition domain may be produced and screened by methods well-known in the art, and also by the methods described by *Current Protocols in Molecular Biology* (1987-2007), vols. 1-4, which is hereby incorporated by reference. A mutant or variant of the polynucleotides encoding a recognition domain or a catalytic domain will have 70%, 80%, 90%, 95%, or 99% homology or similarity to the corresponding sequence. Similarly a mutant or variant of the polypeptides forming a catalytic domain or a recognition domain will have 70%, 80%, 90%, 95%, or 99% homology or similarity to the corresponding amino acid sequence. Such mutants or variants may also encode, or be functionally active fragments of, these polypeptide sequences. A variant or mutant of a catalytic domain will exhibit the E3 ligase activity and those of a recognition domain will have the ability to recognize or bind to a substrate or target protein.

Similarity or homology may be determined by an algorithm, such as those described by *Current Protocols in Molecular Biology*, vol. 4, chapter 19 (1987-2007) or by using software or computer programs such as the BestFit or Gap pairwise comparison programs (GCG Wisconsin Package, Genetics Computer Group, 575 Science Drive, Madison, Wis. 53711). BestFit uses the local homology algorithm of Smith and Waterman, Advances in Applied Mathematics 2: 482-489 (1981), to find the best segment of identity or similarity between two sequences. Gap performs global alignments: all of one sequence with all of another similar sequence using the method of Needleman and Wunsch, J. Mol. Biol. 48:443-453 (1970). When using a sequence alignment program such as BestFit, to determine the degree of sequence homology, similarity or identity, the default setting may be used, or an appropriate scoring matrix may be selected to optimize identity, similarity or homology scores. Similarly, when using a program such as BestFit to determine sequence identity, similarity or homology between two different amino acid sequences, the default settings may be used, or an appropriate scoring matrix, such as blosum45 or blosum80, may be selected to optimize identity, similarity or homology scores.

Polynucleotide variants encoding the E3 ligase catalytic domain of those of *Shigella flexneri* IpaH9.8 (SEQ ID NO: 3) or the E3 ligase domain of SspH1 of *Salmonella* (SEQ ID NO: 7) may be characterized by their ability to hybridize under stringent conditions with the complements of SEQ ID NOS: 3 and 7. Alternatively, such variants may be simply isolated from a *Shigella* or *Salmonella* strain. Hybridization conditions may comprise hybridization at 5×SSC at a temperature of about 50 to 68° C. Washing may be performed using 2×SSC, optionally followed by washing using 0.5×SSC. For even higher stringency, the hybridization temperature may be raised to 68° C. or washing may be performed in a salt solution of 0.1×SSC, or both. Other conventional hybridization procedures and conditions may also be used as described by *Current Protocols in Molecular Biology*, (1987-2007), see e.g. Chapter 2. The details of the subject matter described above are incorporated by reference to the corresponding documents cited above.

Proteins belonging to the Ipah superfamily may be identified by database mining of fully or partially sequenced bacterial genomes as proteins exhibiting over 25% sequence identity with the C-terminal domain of IpaH9.8 or any other member of the Ipah superfamily already identified (and shown in FIG. 4) or as protein containing the motif defined as:

Methods for producing chimeric genes encoding fusion proteins or for producing engineered polypeptides such as peptide aptamer derivatives are well known in the art. Fusion proteins may be produced by conventional fusion protein methods, including those incorporated by reference to Chapter 16 of *Current Protocols in Molecular Biology*, vol. 3 (1987-2007). Expression is not limited to eukaryotic cells such as yeast, plant, insect or mammalian cells, but include expression in prokaryotes, such as enterobacteria, e.g., *E. coli*, *Shigella*, or *Salmonella*. Polypeptide constructs containing a catalytic and recognition domain may also be produced by chemical synthesis or by conjugation of separate peptides or polypeptide moieties. Methods for making aptamer constructs are described by Colas et al., PNAS 97(25): 13720, which is incorporated by reference. Methods for purifying engineered proteins, such as fusion proteins, are well-known and are incorporated by reference to Chapter 10 of *Current Protocols in Molecular Biology*, vol. 2 (1987-2007). Such polypeptide constructs will preferably express the E3 ligase catalytic domain at the C-terminal and a recognition polypeptide domain, which binds to a particular substrate protein, at the N-terminal end.

The isolated chimeric polynucleotides may be placed into vectors, such as plasmid or viral vectors. Such vectors may be transfected into cells to express the corresponding polypeptide constructs or fusion proteins. Vectors suitable for introducing and expressing genes and polynucleotides in eukaryotic host cells are well known in the art. Vectors, host cells and expression methods for recombinant expression of proteins are well-known in the art and generally involve inserting DNA sequences encoding a peptide or polypeptide into a vector, transforming a host cell with the vector and expressing the recombinant protein in the transformed host cells. Recombinant expression of proteins is well known in the art, as are suitable vectors and host cells for expressing proteins, such as polypeptide constructs containing an E3 ligase catalytic domain and a recognition domain. Such methods, vectors and host cells are incorporated by reference to Chapter 1, 2, 3 and 9 of *Current Protocols in Molecular Biology*, vol. 1 (1987-2007) and Chapter 16 "Protein Expression" in vol. 3.

Another aspect of the invention is the use of a fusion protein which comprises an E3 ubiquitin ligase catalytic domain and a recognition domain to modulate protein trafficking in a eukaryotic cell. The fusion protein may be expressed by transfecting or transforming a cell with a vector expressing it, or by transport of the fusion protein directly into a cell, as occurs, for example, with bacterial effector proteins such as SspH1. Modulation and control of trafficking can be used to study intracellular phenomena or to up or down-regulate particular biochemical pathways, such as pathways involved in production of recombinant molecules or other desired products, such as particular chemical compounds by a cell line.

The construct or fusion protein of the invention may be used therapeutically to reduce the intracellular levels or reduce the biological activity of intracellular proteins associated with diseases or responsible for various pathological states. By binding to, and ubiquitinating, these intracellular proteins, their amounts and/or biological activities are reduced, and thus the severity of disease or pathology is reduced. By selecting a construct having a recognition domain for an intracellular protein associated with cancer, an autoimmune disease, a genetic disorder or with a pathogen, such as a virus, bacteria, or parasite, intracellular levels of these virulence-associated proteins may be reduced. For example, HMGA proteins are expressed at a high level during embryogenesis, while their expression becomes low to undetectable in adult tissues. High HMGA expression in adult life is associated only with pathological conditions such as carcinomas; antisense HMGA cDNA interferes with tumor growth in vivo; Pierantoni et al., J. Clin. Invest. Doi 10.1172/JCI29852. The constructs of the invention provide a new way to reduce the levels of these proteins without the use of antisense nucleic acids. The constructs of the invention may be introduced into cells through means known in the art, including by their expression within a cell or by introduction of the protein constructs into the cytoplasm. Methods for introduction of proteins into a cell are well-known in the art and are incorporated by reference to *Current Protocols in Molecular Biology* (1987-2007).

Host cell lines or transgenic animals expressing the fusion protein of the invention may also be constructed using methods known in the art and are incorporated by reference to *Current Protocols in Molecular Biology* (1987-2007), vols 1-4, especially vol. 4, chapter 23. Transgenic animals expressing a polypeptide construct containing an E3 ligase catalytic domain linked to a recognition domain may be employed to measure or investigate the effects of reducing intracellular expression of the target molecule recognized by the recognition domain. For instance, a transgenic animal expressing a construct containing a recognition domain for an HMGA protein may be used to evaluate the effects of lowering HMGA levels on carcinoma and other pathologies associated with HMGA expression. Transgenic animals expressing or containing the constructs of the invention may be used in place of animals having knock-out mutations. Beneficially, the expression of a construct of the invention may be placed under control of an inducible promoter that permits the expression of the construct to be turned on and off. This permits a comparison of the effects of lowering the amount of, or reducing the activity of, a particular target protein in the same cell line without the need to construct and compare a knockout mutant.

The invention is also directed to the polynucleotides such as exogenous inserts which are contained in strains JRE36, JRE52, JRE 63 and JRE66, these strains have deposited at CNCM on Feb. 27, 2007 under the numbers I-3717, I-3718, I-3719 and I-3720.

The invention is also directed to methods of screening molecules, such as putative antimicrobial compounds, for their ability to inhibit E3 ligase activity of IpaH superfamily members, such as those expressed by *Shigella* and *Salmonella*. This method involves (a) contacting an IpaH superfamily E3 ubiquitin ligase with a test molecule in the presence of a substrate protein, ubiquitin, a ubiquitin activating enzyme (E1) and a ubiquitin conjugating enzyme (E2) for a time and under conditions suitable for ubiquitination of the substrate protein recognized by the E3 ubiquitin ligase. The ligase may be a fusion protein comprising a catalytic domain of an IpaH superfamily E3 ubiquitin ligase and a recognition domain for a particular substrate protein. The ability of a test molecule to modulate, e.g., inhibit, the E3 ligase is determined by comparing the amount of ubiquitinated substrate protein in the presence of and absence of the test molecule. Methods and kits for determining ubiquitin protein ligase (E3) activity are known in the art and are incorporated by reference to US2006/008901 A1, WO02/16633 A2 or WO 2004/038036 A2.

Large-scale two-hybrid screens and proteonomics analysis are used to unravel and understand the network of interactions between cellular proteins. However, the functional significance of these interactions is often not understood. As an alternative to the use of siRNA to decrease the translation and stability of mRNA encoding a target protein X, the amount of target protein X can be decreased by using a protein construct of the invention which has a recognition domain for protein X and which reduces it's the amount or activity of protein X through ubiquitinating it. For example, the known binding partner Y of target protein X may be used to form a construct with an IpaH superfamily E3 ubiquitin ligase domain and the polynucleotide encoding this construct transfected into a cell to modulate cellular expression or activity of protein X.

The two-hybrid method in yeast is widely used to characterize or identify protein interactions, see e.g., *Analysis of Protein Interactions*, Chapter 20, *Current Protocols in Molecular Biology* (1989-2007). The classical scheme is based on the reconstitution of a functional transcription factor and relies on protein interactions between (i) a bait consisting of a DNA binding domain of a transcription factor activator fused to the protein of interest (target protein X) and (ii) a prey consisting of an active domain for the transcription factor activator fused to the putative partner(s) of interaction for target protein X. The interaction must occur in the nucleus to lead to activation of the transcription of a gene encoding a selectable marker. As an alternative to this method, the polypeptide constructs of the invention may be used as follows.

A bait construct (i) containing target protein X (or a functional portion or domain of X) fused on the N-terminal end of a counterselectable protein whose activity impairs the growth of yeast on a particular medium. An example of such a counterselectable marker is the product of the URA3 gene that is toxic on a medium containing 5-fluoro-orotic acid (5-FOA). Alternatively, other proteins which are toxic when expressed in yeast, such particular bacterial proteins, may be used. A prey (ii) containing an IpaH superfamily E3 ligase domain on its C-terminal end and a putative binding partner for X (protein Y) (or libraries of protein domains or peptides or peptide aptamers) is constructed.

The interaction between X and Y places the E3 catalytic domain in close proximity to the counterselectable protein, leading to modification and inactivation or degradation of the counterselectable protein. This permits a positive selection of yeast clones in which there is an interaction between X and Y, since binding of X and Y inactivates the toxic counterselectable protein. An advantage of this system is that the interaction of the bait and prey does not need to occur in the nucleus (as with a SiRNA system). Thus, the interaction between cytoplasmic or even membrane proteins can be investigated. A similar system may be employed to study or identify compounds with pharmacological utilities by selecting lead compounds that would interfere with the interaction of X and Y, using, for example, URA3 as a positive selection marker in conjunction with an appropriate medium.

Since ubiquitin-mediated proteolysis has been associated with microbial virulence, the invention also encompasses testing molecules in vitro or in vivo expressing an IpaH superfamily E3 ubiquitin ligase for their ability to inhibit proteolysis of a substrate protein or for their ability to modulate cellular inflammatory responses. The fusion proteins of the present invention which exhibit E3 ligase activity may be employed in such assays. Such methods are incorporated by reference to WO02/16633 A2 or WO 2004/038036 A2.

BRIEF DESCRIPTION OF THE DRAWINGS

FIGS. 4A, B and C shows the amino acid sequence of IpAH from *Shigella flexneri* (SEQ ID NO: 4).

Figure 1:
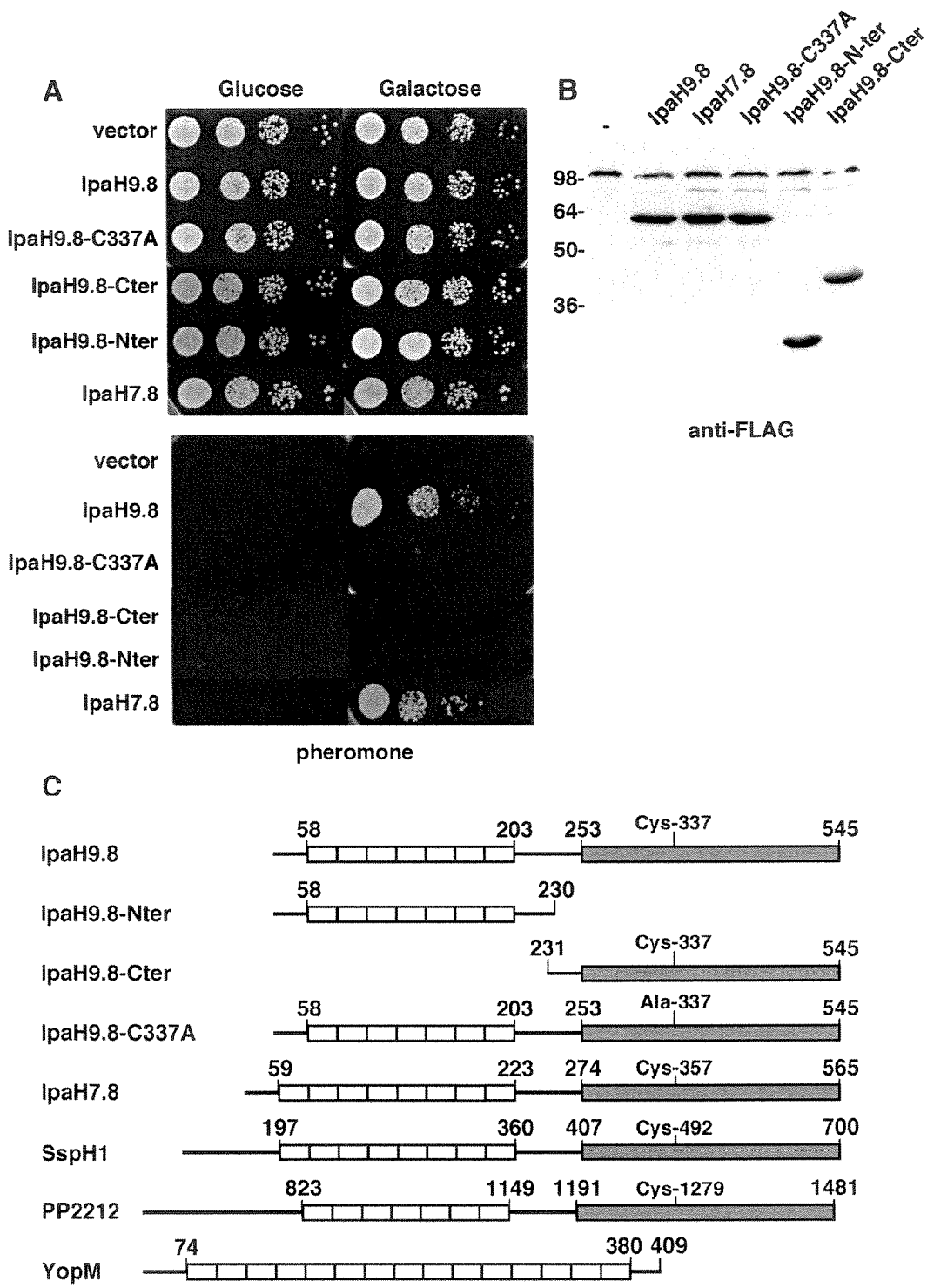
FIG. 1. Functional analysis of IpaH proteins in sst2Δ yeast and domain organization of IpaHs and homologous proteins. (A) Growth on glucose- or galactose-containing plates of serial dilutions of sst2Δ yeast harbouring plasmids encoding indicated proteins; the lower panel shows plates containing α-factor. (B) Immunoblot analysis using anti-FLAG antibodies of extracts of sst2Δ yeast producing indicated FLAG-tagged IpaH proteins. (C) Schematic representation (not to scale) of *S. flexneri* IpaH9.8 and IpaH7.8, *S. enterica* SspH1, *P. putida* PP2212, and *Yersinia* spp. YopM; LRRs and conserved C-terminal domains are shown by open and solid boxes, respectively, and residue positions are indicated by numbers.

The patent or application file contains at least one drawing executed in color. Copies of this patent or patent application publication with color drawing(s) will be provided by the office.

DETAILED DESCRIPTION OF THE INVENTION

IpaH9.8 and SspH1 have been discovered to exhibit E3 ubiquitin ligase activity. In addition to ubiquitin, a yeast substrate for IpaH9.8 (Ste7) and a mammalian substrate for SspH1 (PKN1) were identified. Ubiquitin was removed from ubiquitinated UbcH5B upon incubation with IpaH9.8 or SspH1; this latter activity corresponding to the hydrolysis of the thioester bond linking ubiquitin to the E2 is not equivalent to the activity of de-ubiquitinating enzymes hydrolyzing the amide bond linking ubiquitin to target proteins (Amerik and Hochstrasser, 2004).

It might correspond either to the total consumption of the ubiquitinated E2 by the polyubiquitination activity of IpaH9.8 and SspH1 towards ubiquitin or to the transfer of ubiquitin onto IpaH9.8 and SspH1 prior to its transfer onto the substrate, as described for HECT-domain E3s (Ardley and Robinson, 2005; Scheffner et al., 1995). Although the latter hypothesis is consistent with the observation that the Cys residue conserved in all IpaH family members is required for IpaH9.8 activities both in yeast and in vitro, ubiquitin-IpaH9.8 and ubiquitin-SspH1 intermediates could not be detected. The HECT domain of E3s and the C-terminal domain of IpaH proteins do not share sequence similarities; furthermore, residues surrounding the catalytic Cys residue in HECT-domain E3s and the conserved Cys residue in Ipah proteins are different. Accordingly, IpaH superfamily members constitute a novel class of E3 ubiquitin ligases.

Co-opting the ubiquitination pathway, either to promote or prevent ubiquitination of host proteins, is emerging as a common strategy employed by pathogens using T3S systems to down regulate host responses. The effector AvrPtoB from the tomato pathogen *P. syringae* is structurally similar to U-box and RING-finger E3s, possesses autoubiquitination and presumably ubiquitin ligase activities towards host proteins, and blocks signalling cascades that limit infection by activating the cell death program (Abramovitch et al., 2006; Janjusevic et al., 2006). Through an unknown mechanism, the *P. syringae* effector HopM1 promotes the proteasome-dependent degradation of the *Arabidopsis* protein AtMIN7 and inhibits vesicle trafficking required to mount a cell wall-based defense to infection (Nomura et al., 2006). The *Salmonella* effector SopA has recently been shown to be a HECT-like E3 endowed with an autoubiquitination activity (Zhang et al., 2006). The *Shigella* effector OspG, encoded in the same operon as ipaH9.8, is a kinase that binds ubiquitinated E2s, prevents ubiquitination of phospho-I□B□ and dampens inflammation in the host (Kim et al., 2005). As shown here, the *Salmonella* effector SspH1 is an E3 ubiquitin ligase for PKN1, a protein kinase involved in the NF-κB pathway and activated upon cell infection (Haraga and Miller, 2006). The *S. flexneri* chromosomally-encoded IpaH proteins have been reported to play a role in dampening inflammation (Ashida et al., 2007). The LRR-containing N-terminal domain of IpaHs is likely involved in protein-protein interactions and substrate recognition; the *Yersinia* effector YopM containing only LRRs related to those of IpaHs (FIG. 2C) can act as a scaffolding protein that brings host kinases together (McDonald et al., 2003) and the LRR domain of SspH1 interacts with PKN1 (Haraga and Miller, 2006). In HeLa cells infected by *S. flexneri* for 90 min, a significant decrease in the amount of the MAPKK Mek1, Mek3, and IKKα was not observed, suggesting that these proteins are not degraded upon invasion of epithelial cells. The substrates of IpaH proteins in human cells remain to be identified.

The demonstration that IpaH9.8 and SspH1 are E3 ubiquitin ligases permits determination of the function of these proteins and their homologues during infection by identifying their target(s), possibly protein kinases, in host cells. *Shigella* produces multiple IpaHs that differ in their LRR domain and, likewise, some other pathogens contain several genes encoding IpaH homologues. This diversity suggests that each of these pathogens uses a repertoire of E3 ubiquitin ligases to promote degradation of several host proteins.

EXAMPLES

Many bacteria pathogenic for plants or animals, including *Shigella* spp. responsible for shigellosis in humans, use a type III secretion apparatus to inject effector proteins into host cells. Effectors alter cell signalling and host responses induced upon infection, however, their activities have been elucidated in very few cases. Utilizing *Saccharomyces cerevisiae* as a surrogate host, the Examples below show that the *Shigella* effector protein IpaH9.8 interrupts pheromone response signalling by promoting the proteasome-dependent destruction of the MAPKK Ste7. In vitro, IpaH9.8 displayed ubiquitin ligase activity towards ubiquitin and Ste7.

Replacement of a Cys residue invariant among IpaH homologues of plant and animal pathogens abolished IpaH9.8 activities.

The Examples also show that the IpaH homologue SspH1 from *Salmonella enterica* can ubiquitinate ubiquitin and PKN1, a previously identified partner of interaction of SspH1. These results demonstrate that IpaH superfamily members constitute a novel class of E3 ubiquitin ligases.

Example 1

IpaH9.8 Inhibits the Pheromone Response MAPK Pathway

To gain insight to IpaH9.8 activity, *Saccharomyces cerevisiae* was employed as a surrogate model. Yeast producing FLAG-tagged IpaH9.8 under the control of the GAL promoter were not impaired in their ability to grow at elevated temperatures, in the presence of a variety of ions, or under high and low osmotic stresses. Detection of mating pheromone by a G protein-coupled receptor activates an archetypal MAPK signalling cascade, inducing both arrest of the cell cycle and transcription of mating genes. The pheromone α-factor diffusing from a disk causes cell cycle arrest in MATα cells, resulting in a halo of inhibited growth (Hoffman et al., 2002). Upon exposure to α-factor, wild-type yeast producing IpaH9.8 failed to form a halo and to induce expression of a pheromone-responsive FUS1-lacZ reporter gene, indicating that IpaH9.8 interferes with the pheromone response pathway and acts on or upstream of the MAPK Fus3.

To identify the target of IpaH9.8, yeast strains were used that were altered in the signalling cascade. Overproduction of the G protein α subunit Ste4 activates the signalling pathway and promotes growth arrest (Cole et al., 1990); production of IpaH9.8 rescued this phenotype, i.e. allowed growth, indicating that IpaH9.8 acts downstream of Ste4. The constitutively active variant of the MAPKKK Ste11 encoded by the allele STE11-4 promotes elevated transcription of pheromone responsive genes, even in the absence of pheromone (Stevenson et al., 1992). Growth of the strain SY2625 harbouring a FUS1-HIS3 pheromone-inducible reporter is dependent on signalling through the pheromone response pathway on a medium lacking histidine and containing 3-amino triazole (Evangelista et al., 1997). SY2625 containing a plasmid encoding Ste11-4, but not those containing the vector, were His⁺, consistent with activation of the pathway by Ste11-4 and transcription of FUS1-HIS3. In contrast, yeast containing plasmids encoding Ste11-4 and IpaH9.8 were His⁻, indicating that IpaH9.8 interrupts signalling at or downstream of Ste11, on either the MAPK Fus3 or the MAPKK Ste7. Immunoblot analysis indicated that the amount of Ste7, but not of Ste11 and Fus3, was drastically reduced in wild-type yeast producing IpaH9.8, regardless of stimulation by α-factor. Upon phosphorylation by Ste11, Ste7 is ubiquitinated and, following removal of ubiquitin chains by the specific deubiquitinase Ubp3, is degraded by the proteasome (Wang et al., 2003). In both ubp3Δ, and ste11Δ cells, production of IpaH9.8 still resulted in the disappearance of Ste7, indicating that IpaH9.8-mediated disappearance of Ste7 is independent of the known Ste7 degradation pathway.

Example 2

Structure and Function of IpaH Family Members

Blockage of signalling downstream of Ste11 suggested that IpaH9.8 should rescue sst2Δ cells defective for the GTPase activating protein encoded by SST2; these cells are unable to dampen signalling and can not grow in the presence of pheromone (Dohlman et al., 1996). Indeed, production of IpaH9.8 allowed sst2Δ cells to grow in the presence of pheromone (FIGS. 1A and 1B). IpaH7.8, another IpaH family member from *Shigella*, also rescued the pheromone-induced growth arrest of sst2Δ cells (FIG. 1A), indicating that IpaH9.8 and IpaH7.8 have similar activities in yeast.

The strong phenotype of sst2Δ cells producing IpaH proteins was used to perform a functional analysis of IpaH domains. The nine different IpaHs encoded by the virulence plasmid and the chromosome (Yang et al., 2005) consist of a ≈250-residue variable N-terminal domain containing six to eight 20-residue leucine-rich repeats (LRR) and a ≈300-residue conserved C-terminal domain. Production of neither IpaH9.8-Nter nor IpaH9.8-Cter (FIG. 1C) rescued growth of sst2Δ cells exposed to pheromone (FIG. 1A), indicating that both domains of IpaH9.8 are required for the function in yeast.

Figure 2:
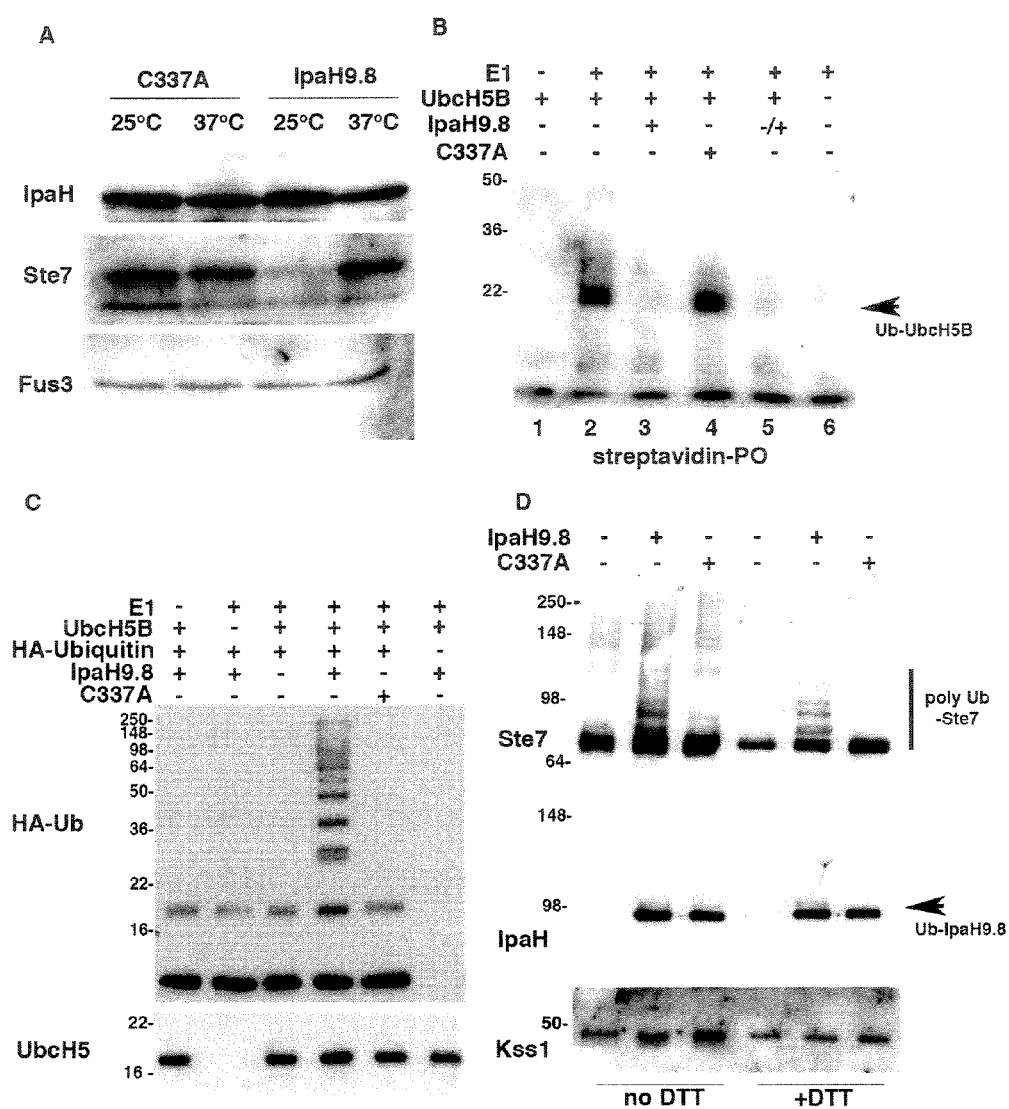
FIG. 2. IpaH9.8 is an E3 ubiquitin ligase. (A) Immunoblot analysis using anti-FLAG, anti-Ste7, and anti-Fus3 antibodies of extracts of cim5-1 yeast producing FLAG-tagged IpaH9.8-C337A (C337A) or IpaH9.8 at 25° C. or 37° C. (B) Immunoblot analysis using streptavidin-peroxidase of reactions performed in the presence of biotinylated ubiquitin, E1, UbcH5B, and either GST-IpaH9.8 (IpaH9.8) or GST-IpaH9.8-C337A (C337A). For the sample loaded in lane 5, GST-IpaH9.8 was added after UbcH5B ubiquitination and the reaction mixture was further incubated for 30 min. (C) Immunoblot analysis using anti-HA and anti-UbcH5 of reactions performed in the presence of HA-ubiquitin, E1, UbcH5B, and either GST-IpaH9.8 (IpaH9.8) or GST-IpaH9.8-C337A (C337A). (D) Immunoblot analysis using anti-Ste7, anti-IpaH, and anti-Kss1 antibodies of reactions performed in the presence of ubiquitin, E1, UbcH5B, GST-IpaH9.8 (IpaH9.8) or GST-IpaH9.8-C337A (C337A), as indicated, and a complex containing Ste7, Ste11-4, and Kss1. Samples were treated or not with DTT prior to loading.

Sequence comparisons revealed that the IpaH C-terminal domain shares 25-40% identity with two groups of proteins of bacteria that contain a T3S system and are pathogens of plants, fish, and mammals (FIG. 4). One group includes eighteen ≈600-residue proteins from *Shigella* spp., *Yersinia pestis* (and *Y. pseudotuberculosis*), *Salmonella enterica*, *Edwardsiella ictaluri*, *Bradyrhizobium japonica*, and *Rhizobium* sp. strain NGR234 and the other includes fifteen ≈1500-residue proteins from *Pseudomonas putida*, *P. entomophila*, *P. fluorescens*, and *P. syringae*. In both groups, the conserved domain is C-terminal and preceded by LRRs (FIG. 2C).

The presence of one Cys residue among the nine residues that are identical in all members of the IpaH family suggested that its thiol group might be involved in catalysis. To test this hypothesis, Cys-337 of IpaH9.8 was replaced by Ala in IpaH9.8-C337A. Although IpaH9.8-C337A was produced in similar amounts to IpaH9.8 (FIG. 1B), it did not allow sst2Δ cells to grow in the presence of pheromone (FIG. 1A). Circular dichroism measurements in the far-UV and near-UV regions on purified GST-IpaH9.8 and GST-IpaH9.8-C337A showed that these two proteins have similar secondary and tertiary structure contents, suggesting that the Cys residue conserved in all IpaH homologues is involved in function rather than in structure.

Example 3

IpaH-Mediated Disappearance of Ste7 is Proteasome Dependent

To test if the IpaH-mediated disappearance of Ste7 required proteasome function, a yeast strain carrying the cim5-1 allele encoding a component of the 26-S proteasome that is functional at 25° C. but not at 37° C. (Ghislain et al., 1993) was used. Ste7 was present in cim5-1 yeast producing IpaH9.8-C337A at both temperatures and IpaH9.8 at 37° C. but was not present in yeast producing IpaH9.8 at 25° C. (FIG. 3A). Moreover, the proteasome inhibitor MG132 prevented the disappearance of Ste7 provoked by IpaH9.8 in a MG132-permeable erg6Δ mutant (Lee and Goldberg, 1998). Thus, the disappearance of Ste7 promoted by IpaH9.8 is proteasome-dependent.

Example 4

IpaH9.8 is an E3 Ubiquitin Ligase for Ste7

The observation that the degradation of Ste7 promoted by IpaH9.8 is proteasome-dependent led us to test in vitro if IpaH9.8 might be involved in an ubiquitination pathway. It was discovered that the E2 enzyme UbcH5B was apparently not ubiquitinated by E1 in the presence of GST-IpaH9.8 (FIG. 2B). Furthermore, after ubiquitination of UbcH5B, addition of GST-IpaH9.8 to the reaction mixture promoted the removal of ubiquitin from UbcH5B (FIG. 3B). This activity was not observed when GST-IpaH9.8-C337A was added to the reaction mixture (FIG. 2B), indicating that it required the Cys residue of IpaH9.8.

The amide linkage, but not the thioesther linkage, of ubiquitin to ubiquitinated proteins is resistant to dithiothreitol (DTT). In reactions containing IpaH9.8, but not in those containing IpaH9.8-C337A or lacking UbcH5B, a DTT-resistant ubiquitinated protein of the size of GST-IpaH9.8 (FIG. 3) was detected. Since some E3 ubiquitin ligases possess an autoubiquitination activity (Beaudenon et al., 2005), these results indicate that IpaH9.8 is an E3 ubiquitin ligase.

Ubiquitin biotinylated on Lys residues can not support polyubiquitination reactions. To test if IpaH9.8 could polyubiquitinate proteins, reactions were performed using HA-tagged ubiquitin, instead of biotinylated ubiquitin. Anti-HA antibodies detected a ladder of ubiquitinated proteins, from 24 to >200 kDa, in reactions performed in the presence of GST-IpaH9.8, but not in the presence of GST-IpaH9.8-C337A (FIG. 3C). Anti-UbcH5B antibodies detected a single species corresponding to UbcH5B (18 kDa), indicating that UbcH5B was not polyubiquitinated (FIG. 2C). The sizes of species detected by anti-HA antibodies were multiples of the size of HA-ubiquitin (9 kDa), indicating that the molecule that was polyubiquitinated is ubiquitin. Using K48R and K63R ubiquitin variants, it was found that IpaH9.8 catalyzed the formation of polyubiquitin chains on Lys-48, but not Lys-63. Polyubiquitinated proteins using the E2 UbcH7 were not detected. These results demonstrate that IpaH9.8 is endowed with ubiquitin ligase activity towards ubiquitin and uses UbcH5B, but not UbcH7, as an E2.

To test whether IpaH9.8 might ubiquitinate Ste7, purified active MAPK complexes containing Ste7, as well as Ste11-4 and the MAPK Kss1, were incubated with native ubiquitin, E1, UbcH5B, and GST-IpaH9.8 or GST-IpaH9.8-C337A. Both the non- and mono-ubiquitinated forms of IpaH9.8 were detected using anti-IpaH antibodies (FIG. 2D), confirming the autoubiquitination activity of IpaH9.8. In addition to Ste7, larger species that formed only in the presence of IpaH9.8 were detected by anti-Ste7 antibodies (FIG. 2D). Thus, IpaH9.8 is an E3 ubiquitin ligase for Ste7; the proteasome-dependent disappearance of Ste7 in yeast was likely due to the degradation of Ste7 following its polyubiquitination by IpaH9.8 and IpaH7.8.

Example 5

The Ipah Homologue SspH1 is an E3 Ubiquitin Ligase for PKN1

Figure 3:
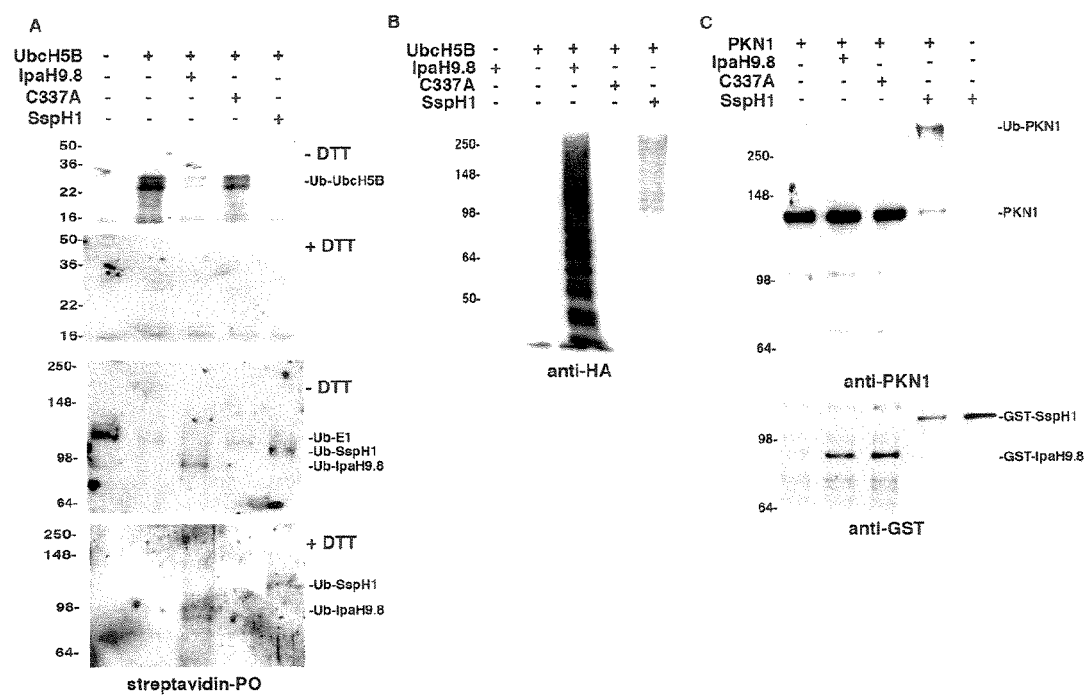
FIG. 3. SspH1 is an E3 ubiqitin ligase. (A) Immunoblot analysis using streptavidin-peroxidase (streptavidin-PO) of reactions performed in the presence of biotinylated ubiquitin, E1, UbcH5B, and either GST-IpaH9.8 (IpaH9.8), GST-IpaH9.8-C337A (C337A), or GST-SspH1 (SspH1). The two upper panels correspond to 15% SDS-PAGE and the two lower panels correspond to 8% SDS-PAGE. Samples were treated or not with DTT prior to loading, as indicated. (B) Immunoblot analysis using anti-HA antibodies of reactions performed in the presence of HA-ubiquitin, E1, UbcH5B, and either GST-IpaH9.8 (IpaH9.8), GST-IpaH9.8-C337A (C337A), or GST-SspH1 (SspH1). (C) Immunoblot analysis using anti-PKN1 and anti-GST antibodies of reactions performed in the presence of ubiquitin, E1, UbcH5B, GST-PKN1 (PKN1) and either GST-IpaH9.8 (IpaH9.8), GST-IpaH9.8-C337A (C337A), or GST-SspH1 (SspH1).
Figure 5:
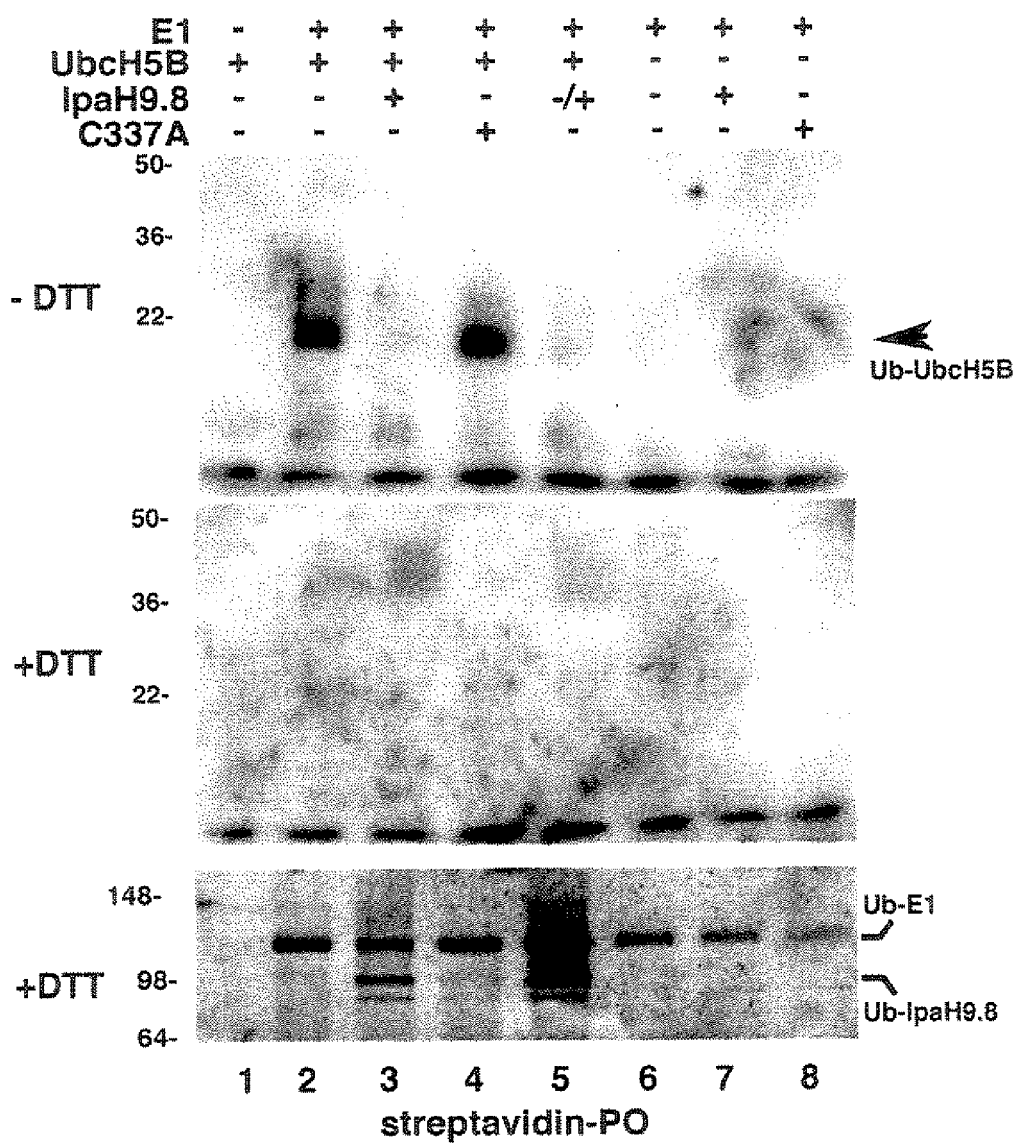
FIG. 5. IpaH9.8 can remove ubiquitin from E2 enzymes and possesses autoubiquitination activity. Immunoblot analysis using peroxidase-coupled streptavidin (streptavidin-PO) of reactions performed in the presence of biotinylated ubiquitin, E1, UbcH5B, and either GST-IpaH9.8 (IpaH9.8) or GST-IpaH9.8-C337A (C337A), as indicated. For the sample loaded in lane 5, GST-IpaH9.8 was added after UbcH5B ubiquitination and the reaction mixture was further incubated for 30 min. Before loading, samples were either treated (middle and bottom panels) or untreated (top panel) with DTT. The top and middle panels correspond to a 15% SDS/PAGE and the bottom panel corresponds to a 10% SDS/PAGE. The position of ubiquitinated UbcH5B, ubiquitinated E1, and ubiquitinated IpaH9.8 is indicated on the right side of panels.

SspH1, one of the *Salmonella enterica* Typhimurium homologues of IpaH, has been shown to interact with the mammalian protein kinase PKN1 (Haraga and Miller, 2006). To test whether SspH1 shares activities with IpaH9.8, a GST-SspH1 recombinant protein was purified. As described above for IpaH9.8, SspH1 was endowed with the activities (i) to remove ubiquitin from ubiquitinated UbcH5B, (ii) to autoubiquitinate, (iii) and to polyubiquitinate HA-tagged ubiquitin (FIG. 3). Ubiquitination of PKN1 by SspH1; SspH1, IpaH9.8, or IpaH9.8-C337A was incubated with E1, native ubiquitin, UbcH5B, and GST-PKN1 was tested. When the reaction was performed in the presence of SspH1, anti-PKN1 antibodies detected an additional species migrating at a size >250 kDa (FIG. 3C). These results demonstrated that SspH1 is an E3 ubiquitin ligase that can use both ubiquitin and PKN1 as substrates.

Experimental Procedures

Materials

Plasmids encoding FLAG-tagged IpaH9.8, IpaH9.8-C337A, IpaH9.8-Cter, IpaH9.8-Nter, and IpaH7.8 were derivatives of the vector pFL38CII/pGal1 containing the GAL promoter (Badis et al., 2004). YCp50-STE11-4 carrying STE11-4 under the control of its own promoter and pRS316-GAL-STE4 carrying STE4 under the control of the GAL promoter have been described (Dohlman et al., 1995; Stevenson et al., 1992). Yeast strains are described in Table S1. UbcH7, E1, ubiquitin, HA-ubiquitin, biotinylated ubiquitin, ubiquitin-K48R and -K63R, horseradish peroxidase-coupled avidin, MG132, and anti-UbcH5 antibodies were purchased from Boston Biochem. Anti-IκBα, -ubiquitin, -Ste7, -Fus3, -Mek3, -I_Kα, -Kss1, and -PKN1 antibodies were purchased from Santa Cruz Biotechnology. Purified GST-PKN1 was purchased from Invitrogen. Anti-Mek1 antibodies and purified active Mek1 were purchased from Upstate Cell Signaling Solutions. The mating pheromone α-factor was purchased from Sigma. His-tagged UbcH5B was prepared as described (Kim et al., 2005). GST-IpaH9.8, GST-IpaH9.8-C337A, and GST-SspH1 were prepared as described (Mavris et al., 2002). Complexes containing Ste11-4, Ste7, and Kss1 were prepared as described (Breitkreutz et al., 2001) and eluted from FLAG M2-agarose affinity gel (Sigma) using a FLAG peptide.

In Vitro Assays

Ubiquitination of UbcH5B-His by E1 was performed in a 40-μl reaction mixture containing buffer A (25 mM Tris.HCl (pH 7.5), 50 mM NaCl, 5 mM ATP, 10 mM $MgCl_2$, 0.1 mM DTT), 2 μg of biotinylated ubiquitin, 0.5 μg of E1, and 2 μg of E2 in the presence, or not, of 1 μg of GST-IpaH9.8, GST-IpaH9.8-C337A, or GST-SspH1. Reactions were incubated at 37° C. for 1 h and stopped by the addition of an equal volume of Laemmli sample buffer (62.5 mM Tris-Hcl, pH 6.8, 10% glycerol, 2% SDS, 0.0005% bromophenol blue) containing, or not, 100 mM DTT. Ubiquitination reactions were carried out in the same manner except that 2 μg of HA-tagged ubiquitin, ubiquitin, ubiquitin-48R or -3R were used instead of biotinylated ubiquitin. Approximately 1 μg of Ste11-4:Ste7:Kss1 complexes, or 0.4 μg of GST-PKN1, was incubated in buffer A with 5 μg of ubiquitin, 0.5 μg of E1, and 2 μg of E2 in the presence, or not, of 0.6 μg of GST-IpaH9.8, GST-IpaH9.8-C337A, or GST-SspH1. Reaction mixtures were separated by SDS/PAGE, transferred onto a nitrocellulose membrane and probed with specific antibodies or peroxidase-coupled streptavidin when biotinylated ubiquitin was used.

Additional Experimental Procedures

Plasmids

DNA fragments encoding IpaH9.8, IpaH9.8-Nter, IpaH9.8-Cter, and IpaH7.8 were amplified by PCR and cloned as XbaI-NotI fragments into the vector pFL38CII/pGal1 containing the GAL promoter (Badis et al., 2004) to create plasmids pJR001, pJR002, pJR003, and pJR004, respectively. The 3' oligonucleotides encoded the FLAG epitope followed by a stop codon and a XbaI site. YCp50-STE11-4 carrying STE11-4 under the control of its own promoter and pRS316-GAL-STE4 carrying STE4 under the control of the GAL promoter have been described (Dohlman et al., 1995; Stevenson et al., 1992). An EcoRI-SpeI fragment from pJR001 encompassing the GAL promoter and the sequence encoding IpaH9.8 and the FLAG tag was cloned into plasmid pRS425 (Sikorski and Hieter, 1989) to create pJR005. Site directed mutagenesis of ipaH9.8 codon 337 (TGT encoding Cys) carried by plasmid pRT7 (Mavris et al., 2002) encoding GST-IpaH9.8 was performed using a Stratagene Quick Change II kit to create plasmid pJR006 encoding the IpaH9.8-C337A variant (GCT encoding Ala). To construct pJR007 encoding IpaH9.8-FLAG, a NdeI-PvuII fragment from pJR006 was transformed into yeast BY4741 along with BsaBI-BsiWI digested pJR001 and transformants were plated on Ura-medium; plasmids were rescued from Ura+ prototrophs. To construct pJR008 encoding GST-SspH1, a the sspH1 gene was amplified by PCR from *Salmonella typhimurium* ATCC 14028 and cloned as a BamHI-XhoI fragment into the vector pGEX-6P1. All plasmid insertions were confirmed by DNA sequencing.

Strains

Invasive wild-type *Shigella flexneri* 5 M90T-Sm (Allaoui et al., 1992) and its mxiE derivative SF1060 (Mavris et al., 2002) were used for infection. Plasmids were propagated in *Escherichia coli* DH5α (end A1 hsdR17 sup E44 thi1 recA1 gyrA relA1 lacZYA-argF). To create JRY101, the integrating plasmid pFC23 (O'Rourke and Herskowitz, 1998) containing a FUS-lacZ transcriptional fusion was digested with SphI and transformed into BY4741; Leu+ colonies were tested for pheromone-responsive β-galactosidase production. JRY100 was constructed by PCR-mediated gene disruption in strain BY4741, replacing the entire open reading frame of UBP3 by the Nat marker, as described (Goldstein and McCusker, 1999; Longtine et al., 1998); the gene replacement was confirmed by PCR.

Yeast Manipulations

Standard media and techniques were used for transformation, maintenance, and growth of yeast (Guthrie C, 1991). Halo assays were performed as described (Hoffman et al., 2002) using disks impregnated with 15 μg of α-factor. erg6Δ yeast were transformed with plasmids encoding IpaH9.8 or IpaH9.8-C337A and grown in selective media containing 1% raffinose to mid log phase. Following addition of MG132 (100 μM) and galactose (2%), cultures were incubated for 2 h and cell extracts were prepared as described (Wang et al., 2003). β-Galactosidase assays were performed as described (Guarente, 1983).

REFERENCES

Abramovitch, R. B., Janjusevic, R., Stebbins, C. E., and Martin, G. B. (2006). Type III effector AvrPtoB requires intrinsic E3 ubiquitin ligase activity to suppress plant cell death and immunity. Proc. Natl, Acad. Sci. U.S.A. 103, 2851-2856.

Alto, N. M., Shao, F., Lazar, C. S., Brost, R. L., Chua, G., Mattoo, S., McMahon, S. A., Ghosh, P., Hughes, T. R., Boone, C., and Dixon, J. E. (2006). Identification of a bacterial type III effector family with G protein mimicry functions. Cell 124, 133-145.

Amerik, A. Y., and Hochstrasser, M. (2004). Mechanism and function of deubiquitinating enzymes. Biochim. Biophys. Acta. 1695, 189-207.

Ardley, H. C., and Robinson, P. A. (2005). E3 ubiquitin ligases. Essays Biochem. 41, 15-30.

Ashida, H., Toyotome, T., Nagai, T., and Sasakawa, C. (2007). *Shigella* chromosomal IpaH proteins are secreted via the type III secretion system and act as effectors. Mol. Microbiol. 63, 680-693.

Badis, G., Saveanu, C., Fromont-Racine, M., and Jacquier, A. (2004). Targeted mRNA degradation by deadenylation-independent decapping. Mol. Cell. 15, 5-15.

Beaudenon, S., Dastur, A., and Huibregtse, J. M. (2005). Expression and assay of HECT domain ligases. Methods Enzymol. 398, 112-125.

Breitkreutz, A., Boucher, L., and Tyers, M. (2001). MAPK specificity in the yeast pheromone response independent of transcriptional activation. Curr. Biol. 11, 1266-1271.

Cole, G. M., Stone, D. E., and Reed, S. I. (1990). Stoichiometry of G protein subunits affects the *Saccharomyces cerevisiae* mating pheromone signal transduction pathway. Mol. Cell. Biol. 10, 510-517.

Demers, B., Sansonetti, P. J., and Parsot, C. (1998). Induction of type III secretion in *Shigella flexneri* is associated with differential control of transcription of genes encoding secreted proteins. Embo J. 17, 2894-2903.

Dohlman, H. G., Apaniesk, D., Chen, Y., Song, J., and Nusskern, D. (1995). Inhibition of G-protein signaling by dominant gain-of-function mutations in Sst2p, a pheromone desensitization factor in *Saccharomyces cerevisiae*. Mol. Cell. Biol. 15, 3635-3643.

Dohlman, H. G., Song, J., Ma, D., Courchesne, W. E., and Thorner, J. (1996). Sst2, a negative regulator of pheromone signaling in the yeast *Saccharomyces cerevisiae*: expression, localization, and genetic interaction and physical association with Gpa1 (the G-protein alpha subunit). Mol. Cell. Biol. 16, 5194-5209.

Evangelista, M., Blundell, K., Longtine, M. S., Chow, C. J., Adames, N., Pringle, J. R., Peter, M., and Boone, C. (1997). Bni1p, a yeast formin linking cdc42p and the actin cytoskeleton during polarized morphogenesis. Science 276, 118-122.

Galan, J. E., and Cossart, P. (2005). Host-pathogen interactions: a diversity of themes, a variety of molecular machines. Curr. Opin. Microbiol. 8, 1-3.

Ghislain, M., Udvardy, A., and Mann, C. (1993). S. cerevisiae 26S protease mutants arrest cell division in G2/metaphase. Nature 366, 358-362.

Haraga, A., and Miller, S. I. (2006). A *Salmonella* type III secretion effector interacts with the mammalian serine/threonine protein kinase PKN1. Cell. Microbiol. 8, 837-846.

Hoffman, G. A., Garrison, T. R., and Dohlman, H. G. (2002). Analysis of RGS proteins in *Saccharomyces cerevisiae*. Methods. Enzymol. 344, 617-631.

Inohara, Chamaillard, McDonald, C., and Nunez, G. (2005). NOD-LRR proteins: role in host-microbial interactions and inflammatory disease. Annu. Rev. Biochem. 74, 355-383.

Janjusevic, R., Abramovitch, R. B., Martin, G. B., and Stebbins, C. E. (2006). A bacterial inhibitor of host programmed cell death defenses is an E3 ubiquitin ligase. Science 311, 222-226.

Kim, D. W., Lenzen, G., Page, A. L., Legrain, P., Sansonetti, P. J., and Parsot, C. (2005). The *Shigella flexneri* effector OspG interferes with innate immune responses by targeting ubiquitin-conjugating enzymes. Proc. Natl. Acad. Sci. U.S.A. 102, 14046-14051.

Lee, D. H., and Goldberg, A. L. (1998). Proteasome inhibitors: valuable new tools for cell biologists. Trends Cell Biol. 8, 397-403.

Liu, Y. C. (2004). Ubiquitin ligases and the immune response. Annu. Rev. Immunol. 22, 81-127.

Mavris, M., Page, A. L., Tournebize, R., Demers, B., Sansonetti, P., and Parsot, C. (2002). Regulation of transcription by the activity of the *Shigella flexneri* type III secretion apparatus. Mol. Microbiol. 43, 1543-1553.

McDonald, C., Vacratsis, P. O., Bliska, J. B., and Dixon, J. E. (2003). The *Yersinia* virulence factor YopM forms a novel protein complex with two cellular kinases. J. Biol. Chem. 278, 18514-18523.

Menard, R., Sansonetti, P., and Parsot, C. (1994). The secretion of the *Shigella flexneri* Ipa invasins is activated by epithelial cells and controlled by IpaB and IpaD. Embo J. 13, 5293-5302.

Nomura, K., Debroy, S., Lee, Y. H., Pumplin, N., Jones, J., and He, S. Y. (2006). A bacterial virulence protein suppresses host innate immunity to cause plant disease. Science 313, 220-223.

Parsot, C. (2005). *Shigella* spp. and enteroinvasive *Escherichia coli* pathogenicity factors. FEMS Microbiol. Lett. 252, 11-18.

Penno, C., Sansonetti, P., and Parsot, C. (2005). Frameshifting by transcriptional slippage is involved in production of MxiE, the transcription activator regulated by the activity of the type III secretion apparatus in *Shigella flexneri*. Mol. Microbiol. 56, 204-214.

Scheffner, M., Nuber, U., and Huibregtse, J. M. (1995). Protein ubiquitination involving an E1-E2-E3 enzyme ubiquitin thioester cascade. Nature 373, 81-83.

Stevenson, B. J., Rhodes, N., Errede, B., and Sprague, G. F., Jr. (1992). Constitutive mutants of the protein kinase STE11 activate the yeast pheromone response pathway in the absence of the G protein. Genes Dev. 6, 1293-1304.

Valdivia, R. H. (2004). Modeling the function of bacterial virulence factors in *Saccharomyces cerevisiae*. Eukaryot. Cell 3, 827-834.

Wang, Y., Ge, Q., Houston, D., Thorner, J., Errede, B., and Dohlman, H. G. (2003). Regulation of Ste7 ubiquitination by Ste11 phosphorylation and the Skp1-Cullin-F-box complex. J. Biol. Chem. 278, 22284-22289.

Yang, F., Yang, J., Zhang, X., Chen, L., Jiang, Y., Yan, Y., Tang, X., Wang, J., Xiong, Z., Dong, J., et al. (2005). Genome dynamics and diversity of *Shigella* species, the etiologic agents of bacillary dysentery. Nucl. Acids. Res. 33, 6445-6458.

Zhang, Y., Higashide, W. M., McCormick, B. A., Chen, J., and Zhou, D. (2006). The inflammation-associated *Salmonella* SopA is a HECT-like E3 ubiquitin ligase. Mol. Microbiol. 62, 786-793.

Allaoui, A., Mounier, J., Prevost, M. C., Sansonetti, P. J., and Parsot, C. (1992). icsB: a *Shigella flexneri* virulence gene necessary for the lysis of protrusions during intercellular spread. Mol. Microbiol. 6, 1605-1616.

Badis, G., Saveanu, C., Fromont-Racine, M., and Jacquier, A. (2004). Targeted mRNA degradation by deadenylation-independent decapping. Mol. Cell. 15, 5-15.

Dohlman, H. G., Apaniesk, D., Chen, Y., Song, J., and Nusskern, D. (1995). Inhibition of G-protein signaling by dominant gain-of-function mutations in Sst2p, a pheromone desensitization factor in *Saccharomyces cerevisiae*. Mol. Cell. Biol. 15, 3635-3643.

Evangelista, M., Blundell, K., Longtine, M. S., Chow, C. J., Adames, N., Pringle, J. R., Peter, M., and Boone, C. (1997). Bni1p, a yeast formin linking cdc42p and the actin cytoskeleton during polarized morphogenesis. Science 276, 118-122.

Ghislain, M., Udvardy, A., and Mann, C. (1993). *S. cerevisiae* 26S protease mutants arrest cell division in G2/metaphase. Nature 366, 358-362.

Goldstein, A. L., and McCusker, J. H. (1999). Three new dominant drug resistance cassettes for gene disruption in *Saccharomyces cerevisiae*. Yeast 15, 1541-1553.

Guarente, L. (1983). Yeast promoters and lacZ fusions designed to study expression of cloned genes in yeast. Methods Enzymol. 101, 181-191.

Guthrie C, F. G. (1991). Methods in Enzymology: Guide to Yeast Genetics and Molecular Biology, Vol 350 (San Diego, Calif., Academic Press).

Hoffman, G. A., Garrison, T. R., and Dohlman, H. G. (2002). Analysis of RGS proteins in *Saccharomyces cerevisiae*. Methods Enzymol. 344, 617-631.

Kim, D. W., Lenzen, G., Page, A. L., Legrain, P., Sansonetti, P. J., and Parsot, C. (2005). The *Shigella flexneri* effector OspG interferes with innate immune responses by targeting ubiquitin-conjugating enzymes. Proc. Natl. Acad. Sci. USA 102, 14046-14051. Longtine, M. S., McKenzie, A., 3rd, Demarini, D. J., Shah, N. G., Wach, A., Brachat, A., Philippsen, P., and Pringle, J. R. (1998). Additional modules for versatile and economical PCR-based gene deletion and modification in *Saccharomyces cerevisiae*. Yeast 14, 953-961.

Mavris, M., Page, A. L., Tournebize, R., Demers, B., Sansonetti, P., and Parsot, C. (2002). Regulation of transcription by the activity of the *Shigella flexneri* type III secretion apparatus. Mol. Microbiol. 43, 1543-1553.

O'Rourke, S. M., and Herskowitz, I. (1998). The Hog1 MAPK prevents cross talk between the HOG and pheromone response MAPK pathways in *Saccharomyces cerevisiae*. Genes Dev. 12, 2874-2886.

Sikorski, R. S., and Hieter, P. (1989). A system of shuttle vectors and yeast host strains designed for efficient manipulation of DNA in *Saccharomyces cerevisiae*. Genetics 122, 19-27.

Stevenson, B. J., Rhodes, N., Errede, B., and Sprague, G. F., Jr. (1992). Constitutive mutants of the protein kinase STE11 activate the yeast pheromone response pathway in the absence of the G protein. Genes Dev. 6, 1293-1304.

Tran Van Nhieu, G., Ben-Ze'ev, A., and Sansonetti, P. J. (1997). Modulation of bacterial entry into epithelial cells by association between vinculin and the *Shigella* IpaA invasin. Embo J 16, 2717-2729.

Wang, Y., Ge, Q., Houston, D., Thorner, J., Errede, B., and Dohlman, H. G. (2003). Regulation of Ste7 ubiquitination by Ste11 phosphorylation and the Skp1-Cullin-F-box complex. J. Biol. Chem. 278, 22284-22289.

INCORPORATION BY REFERENCE

Each document, patent, patent application or patent publication cited by or referred to in this disclosure is incorporated by reference in its entirety. However, no admission is made that any such reference constitutes prior art and the right to challenge the accuracy and pertinency of the cited documents is reserved.

The invention claimed is:

1. A method for identifying a molecule which modulates the ligase activity of a member of the IpaH superfamily E3 ubiquitin ligase containing the sequence Cys-(Xaa)$_n$-Asp (SEQ ID NO: 1), wherein "n" represents at least one up to 20 amino acids, comprising:
    contacting a test molecule with the E3 ubiquitin ligase in the presence of ubiquitin, E1 and E2 and a substrate protein; and
    determining ubiquitination of the substrate protein;
    wherein the E3 ubiquitin ligase is a *Shigella* E3 ubiquitin ligase.

2. The method of claim 1, wherein said E3 ubiquitin ligase is a fusion protein comprising a catalytic domain of an IpaH superfamily E3 ubiquitin ligase and a recognition domain for the substrate protein.

3. The method of claim 1, wherein said E3 ubiquitin ligase comprises SEQ ID NO: 4.

4. The method of claim 1, wherein an ability of the test molecule to inhibit E3 ubiquitin ligase is determined by comparing the amount of ubiquitinated substrate protein produced in the presence and in the absence of the test molecule.

* * * * *

SEQUENCE LISTING

<160> NUMBER OF SEQ ID NOS: 12

<210> SEQ ID NO 1
<211> LENGTH: 22
<212> TYPE: PRT
<213> ORGANISM: Artificial Sequence
<220> FEATURE:
<223> OTHER INFORMATION: IpaH E3 ligase catalytic domain motif
<220> FEATURE:
<221> NAME/KEY: MISC_FEATURE
<222> LOCATION: (2)..(21)
<223> OTHER INFORMATION: Xaa is any amino acid or absent. At least one
      Xaa is present.

<400> SEQUENCE: 1

Cys Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Asp
            20

<210> SEQ ID NO 2
<211> LENGTH: 160
<212> TYPE: PRT
<213> ORGANISM: Artificial
<220> FEATURE:
<223> OTHER INFORMATION: Motif IpaH C-terminal E3 ligase
<220> FEATURE:
<221> NAME/KEY: misc_feature
<222> LOCATION: (2)..(73)
<223> OTHER INFORMATION: Xaa can be any naturally occurring amino acid
      or absent, where at least 59 and up to 72 Xaa are present
<220> FEATURE:
<221> NAME/KEY: misc_feature
<222> LOCATION: (75)..(75)
<223> OTHER INFORMATION: Xaa can be any naturally occurring amino acid
<220> FEATURE:
<221> NAME/KEY: misc_feature
<222> LOCATION: (77)..(107)
<223> OTHER INFORMATION: Xaa can be any naturally occurring amino acid
      or absent, where at least 29 and up to 31 Xaa are present
<220> FEATURE:
<221> NAME/KEY: misc_feature
<222> LOCATION: (109)..(116)
<223> OTHER INFORMATION: Xaa can be any naturally occurring amino acid
<220> FEATURE:
<221> NAME/KEY: misc_feature
<222> LOCATION: (118)..(124)
<223> OTHER INFORMATION: Xaa can be any naturally occurring amino acid
<220> FEATURE:
<221> NAME/KEY: misc_feature
<222> LOCATION: (126)..(147)
<223> OTHER INFORMATION: Xaa can be any naturally occurring amino acid
      or absent, where at least 13 and up to 22 Xaa are present
<220> FEATURE:
<221> NAME/KEY: misc_feature
<222> LOCATION: (149)..(157)
<223> OTHER INFORMATION: Xaa can be any naturally occurring amino acid
<220> FEATURE:
<221> NAME/KEY: misc_feature
<222> LOCATION: (159)..(159)
<223> OTHER INFORMATION: Xaa can be any naturally occurring amino acid

<400> SEQUENCE: 2

Trp Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa
        35                  40                  45

```
Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Cys Xaa Asp Xaa Xaa Xaa Xaa
65                  70                  75                  80

Xaa Xaa Xaa Xaa Xaa Xaa Xaa Xaa Xaa Xaa Xaa Xaa Xaa Xaa
                85                  90                  95

Xaa Xaa Xaa Xaa Xaa Xaa Xaa Xaa Xaa Leu Xaa Xaa Xaa Xaa
            100                 105                 110

Xaa Xaa Xaa Xaa Arg Xaa Xaa Xaa Xaa Xaa Xaa Ala Xaa Xaa Xaa
        115                 120                 125

Xaa Xaa Xaa Xaa Xaa Xaa Xaa Xaa Xaa Xaa Xaa Xaa Xaa Xaa
    130                 135                 140

Xaa Xaa Xaa Leu Xaa Xaa Xaa Xaa Xaa Xaa Xaa Leu Xaa Leu
145                 150                 155                 160

<210> SEQ ID NO 3
<211> LENGTH: 1639
<212> TYPE: DNA
<213> ORGANISM: Shigella flexneri
<220> FEATURE:
<221> NAME/KEY: CDS
<222> LOCATION: (1)..(1638)
<220> FEATURE:
<221> NAME/KEY: misc_feature
<222> LOCATION: (1)..(1638)
<223> OTHER INFORMATION: Shigella IpaH9.8 DNA sequence (JRE 36)

<400> SEQUENCE: 3 atg tta ccg ata aat aat aac ttt tca ttg ccc caa aat tct ttt tat      48
Met Leu Pro Ile Asn Asn Asn Phe Ser Leu Pro Gln Asn Ser Phe Tyr
1               5                   10                  15 aac act att tcc ggt aca tat gct gat tac ttt tca gca tgg gat aaa      96
Asn Thr Ile Ser Gly Thr Tyr Ala Asp Tyr Phe Ser Ala Trp Asp Lys
            20                  25                  30 tgg gaa aaa caa gcg ctc ccc ggt gaa gag cgt gat gag gct gtc tcc     144
Trp Glu Lys Gln Ala Leu Pro Gly Glu Glu Arg Asp Glu Ala Val Ser
        35                  40                  45 cga ctt aaa gaa tgt ctt atc aat aat tcc gat gaa ctt cga ctg gac     192
Arg Leu Lys Glu Cys Leu Ile Asn Asn Ser Asp Glu Leu Arg Leu Asp
    50                  55                  60 cgt tta aat ctg tcc tcg cta cct gac aac tta cca gct cag ata acg     240
Arg Leu Asn Leu Ser Ser Leu Pro Asp Asn Leu Pro Ala Gln Ile Thr
65                  70                  75                  80 ctg ctc aat gta tca tat aat caa tta act aac cta cct gaa ctg cct     288
Leu Leu Asn Val Ser Tyr Asn Gln Leu Thr Asn Leu Pro Glu Leu Pro
                85                  90                  95 gtt acg cta aaa aaa tta tat tcc gcc agc aat aaa tta tca gaa ttg     336
Val Thr Leu Lys Lys Leu Tyr Ser Ala Ser Asn Lys Leu Ser Glu Leu
            100                 105                 110 ccc gtg cta cct cct gcg ctg gag tca ctt cag gta caa cac aat gag     384
Pro Val Leu Pro Pro Ala Leu Glu Ser Leu Gln Val Gln His Asn Glu
        115                 120                 125 ctg gaa aac ctg cca gct tta ccc gat tcg tta ttg act atg aat atc     432
Leu Glu Asn Leu Pro Ala Leu Pro Asp Ser Leu Leu Thr Met Asn Ile
    130                 135                 140 agc tat aac gaa ata gtc tcc tta cca tcg ctc cca cag gct ctt aaa     480
Ser Tyr Asn Glu Ile Val Ser Leu Pro Ser Leu Pro Gln Ala Leu Lys
145                 150                 155                 160 aat ctc aga gcg acc cgt aat ttc ctc act gag cta cca gca ttt tct     528
Asn Leu Arg Ala Thr Arg Asn Phe Leu Thr Glu Leu Pro Ala Phe Ser
                165                 170                 175
```

```
gag gga aat aat ccc gtt gtc aga gag tat ttt ttt gat aga aat cag      576
Glu Gly Asn Asn Pro Val Val Arg Glu Tyr Phe Phe Asp Arg Asn Gln
            180                 185                 190 ata agt cat atc ccg gaa agc att ctt aat ctg agg aat gaa tgt tca      624
Ile Ser His Ile Pro Glu Ser Ile Leu Asn Leu Arg Asn Glu Cys Ser
            195                 200                 205 ata cat att agt gat aac cca tta tca tcc cat gct ctg caa gcc ctg      672
Ile His Ile Ser Asp Asn Pro Leu Ser Ser His Ala Leu Gln Ala Leu
    210                 215                 220 caa aga tta acc tct tcg ccg gac tac cac ggc cca cgg att tac ttc      720
Gln Arg Leu Thr Ser Ser Pro Asp Tyr His Gly Pro Arg Ile Tyr Phe
225                 230                 235                 240 tcc atg agt gac gga caa cag aat aca ctc cat cgc ccc ctg gct gat      768
Ser Met Ser Asp Gly Gln Gln Asn Thr Leu His Arg Pro Leu Ala Asp
                245                 250                 255 gcc gtg aca gca tgg ttc ccg gaa aac aaa caa tct gat gta tca cag      816
Ala Val Thr Ala Trp Phe Pro Glu Asn Lys Gln Ser Asp Val Ser Gln
            260                 265                 270 ata tgg cat gct ttt gaa cat gaa gag cat gcc aac acc ttt tcc gcg      864
Ile Trp His Ala Phe Glu His Glu Glu His Ala Asn Thr Phe Ser Ala
            275                 280                 285 ttc ctt gac cgc ctt tcc gat acc gtc tct gca cgc aat acc tcc gga      912
Phe Leu Asp Arg Leu Ser Asp Thr Val Ser Ala Arg Asn Thr Ser Gly
    290                 295                 300 ttc cgt gaa cag gtc gct gca tgg ctg gaa aaa ctc agt gcc tct gcg      960
Phe Arg Glu Gln Val Ala Ala Trp Leu Glu Lys Leu Ser Ala Ser Ala
305                 310                 315                 320 gag ctt cga cag cag tct ttc gct gtt gct gct gat gcc act gag agc     1008
Glu Leu Arg Gln Gln Ser Phe Ala Val Ala Ala Asp Ala Thr Glu Ser
                325                 330                 335 tgt gag gac cgt gtc gcg ctc aca tgg aac aat ctc cgg aaa acc ctc     1056
Cys Glu Asp Arg Val Ala Leu Thr Trp Asn Asn Leu Arg Lys Thr Leu
            340                 345                 350 ctg gtc cat cag gca tca gaa ggc ctt ttc gat aat gat acc ggc gct     1104
Leu Val His Gln Ala Ser Glu Gly Leu Phe Asp Asn Asp Thr Gly Ala
            355                 360                 365 ctc ctc tcc ctg ggc agg gaa atg ttc cgc ctc gaa att ctg gag gat     1152
Leu Leu Ser Leu Gly Arg Glu Met Phe Arg Leu Glu Ile Leu Glu Asp
    370                 375                 380 att gcc cgg gat aaa gtc aga act ctc cat ttt gtg gat gag ata gaa     1200
Ile Ala Arg Asp Lys Val Arg Thr Leu His Phe Val Asp Glu Ile Glu
385                 390                 395                 400 gtc tac ctg gcc ttc cag acc atg ctc gca gag aaa ctt cag ctc tcc     1248
Val Tyr Leu Ala Phe Gln Thr Met Leu Ala Glu Lys Leu Gln Leu Ser
                405                 410                 415 act gcc gtg aag gaa atg cgt ttc tat ggc gtg tcg gga gtg aca gca     1296
Thr Ala Val Lys Glu Met Arg Phe Tyr Gly Val Ser Gly Val Thr Ala
            420                 425                 430 aat gac ctc cgc act gcc gaa gcc atg gtc aga agc cgt gaa gag aat     1344
Asn Asp Leu Arg Thr Ala Glu Ala Met Val Arg Ser Arg Glu Glu Asn
            435                 440                 445 gaa ttt acg gac tgg ttc tcc ctc tgg gga cca tgg cat gct gta ctg     1392
Glu Phe Thr Asp Trp Phe Ser Leu Trp Gly Pro Trp His Ala Val Leu
    450                 455                 460 aag cgt acg gaa gct gac cgc tgg gcg cag gca gaa gag cag aaa tat     1440
Lys Arg Thr Glu Ala Asp Arg Trp Ala Gln Ala Glu Glu Gln Lys Tyr
465                 470                 475                 480 gag atg ctg gag aat gag tac cct cag agg gtg gct gac cgg ctg aaa     1488
Glu Met Leu Glu Asn Glu Tyr Pro Gln Arg Val Ala Asp Arg Leu Lys
```

-continued

```
                    485                 490                 495
gca tca ggt ctg agc ggt gat gcg gat gcg gag agg gaa gcc ggt gca      1536
Ala Ser Gly Leu Ser Gly Asp Ala Asp Ala Glu Arg Glu Ala Gly Ala
            500                 505                 510 cag gtg atg cgt gag act gaa cag cag att tac cgt cag ctg act gac      1584
Gln Val Met Arg Glu Thr Glu Gln Gln Ile Tyr Arg Gln Leu Thr Asp
        515                 520                 525 gag gta ctg gcc ctg cga ttg tct gaa aac ggc tca caa ctg cac cat      1632
Glu Val Leu Ala Leu Arg Leu Ser Glu Asn Gly Ser Gln Leu His His
    530                 535                 540 tca taa t                                                             1639
Ser
545

<210> SEQ ID NO 4
<211> LENGTH: 545
<212> TYPE: PRT
<213> ORGANISM: Shigella flexneri

<400> SEQUENCE: 4

Met Leu Pro Ile Asn Asn Phe Ser Leu Pro Gln Asn Ser Phe Tyr
1               5                   10                  15

Asn Thr Ile Ser Gly Thr Tyr Ala Asp Tyr Phe Ser Ala Trp Asp Lys
                20                  25                  30

Trp Glu Lys Gln Ala Leu Pro Gly Glu Glu Arg Asp Glu Ala Val Ser
            35                  40                  45

Arg Leu Lys Glu Cys Leu Ile Asn Asn Ser Asp Glu Leu Arg Leu Asp
        50                  55                  60

Arg Leu Asn Leu Ser Ser Leu Pro Asp Asn Leu Pro Ala Gln Ile Thr
65                  70                  75                  80

Leu Leu Asn Val Ser Tyr Asn Gln Leu Thr Asn Leu Pro Glu Leu Pro
                85                  90                  95

Val Thr Leu Lys Lys Leu Tyr Ser Ala Ser Asn Lys Leu Ser Glu Leu
            100                 105                 110

Pro Val Leu Pro Pro Ala Leu Glu Ser Leu Gln Val Gln His Asn Glu
        115                 120                 125

Leu Glu Asn Leu Pro Ala Leu Pro Asp Ser Leu Leu Thr Met Asn Ile
    130                 135                 140

Ser Tyr Asn Glu Ile Val Ser Leu Pro Ser Leu Pro Gln Ala Leu Lys
145                 150                 155                 160

Asn Leu Arg Ala Thr Arg Asn Phe Leu Thr Glu Leu Pro Ala Phe Ser
                165                 170                 175

Glu Gly Asn Asn Pro Val Val Arg Glu Tyr Phe Phe Asp Arg Asn Gln
            180                 185                 190

Ile Ser His Ile Pro Glu Ser Ile Leu Asn Leu Arg Asn Glu Cys Ser
        195                 200                 205

Ile His Ile Ser Asp Asn Pro Leu Ser Ser His Ala Leu Gln Ala Leu
    210                 215                 220

Gln Arg Leu Thr Ser Ser Pro Asp Tyr His Gly Pro Arg Ile Tyr Phe
225                 230                 235                 240

Ser Met Ser Asp Gly Gln Gln Asn Thr Leu His Arg Pro Leu Ala Asp
                245                 250                 255

Ala Val Thr Ala Trp Phe Pro Glu Asn Lys Gln Ser Asp Val Ser Gln
            260                 265                 270

Ile Trp His Ala Phe Glu His Glu Glu His Ala Asn Thr Phe Ser Ala
        275                 280                 285
```

```
Phe Leu Asp Arg Leu Ser Asp Thr Val Ser Ala Arg Asn Thr Ser Gly
    290                 295                 300
Phe Arg Glu Gln Val Ala Ala Trp Leu Glu Lys Leu Ser Ala Ser Ala
305                 310                 315                 320
Glu Leu Arg Gln Gln Ser Phe Ala Val Ala Ala Asp Ala Thr Glu Ser
                325                 330                 335
Cys Glu Asp Arg Val Ala Leu Thr Trp Asn Asn Leu Arg Lys Thr Leu
                340                 345                 350
Leu Val His Gln Ala Ser Glu Gly Leu Phe Asp Asn Asp Thr Gly Ala
                355                 360                 365
Leu Leu Ser Leu Gly Arg Glu Met Phe Arg Leu Glu Ile Leu Glu Asp
    370                 375                 380
Ile Ala Arg Asp Lys Val Arg Thr Leu His Phe Val Asp Glu Ile Glu
385                 390                 395                 400
Val Tyr Leu Ala Phe Gln Thr Met Leu Ala Glu Lys Leu Gln Leu Ser
                405                 410                 415
Thr Ala Val Lys Glu Met Arg Phe Tyr Gly Val Ser Gly Val Thr Ala
                420                 425                 430
Asn Asp Leu Arg Thr Ala Glu Ala Met Val Arg Ser Arg Glu Glu Asn
                435                 440                 445
Glu Phe Thr Asp Trp Phe Ser Leu Trp Gly Pro Trp His Ala Val Leu
    450                 455                 460
Lys Arg Thr Glu Ala Asp Arg Trp Ala Gln Ala Glu Glu Gln Lys Tyr
465                 470                 475                 480
Glu Met Leu Glu Asn Glu Tyr Pro Gln Arg Val Ala Asp Arg Leu Lys
                485                 490                 495
Ala Ser Gly Leu Ser Gly Asp Ala Asp Ala Glu Arg Glu Ala Gly Ala
                500                 505                 510
Gln Val Met Arg Glu Thr Glu Gln Gln Ile Tyr Arg Gln Leu Thr Asp
                515                 520                 525
Glu Val Leu Ala Leu Arg Leu Ser Glu Asn Gly Ser Gln Leu His His
    530                 535                 540
Ser
545

<210> SEQ ID NO 5
<211> LENGTH: 1017
<212> TYPE: DNA
<213> ORGANISM: Shigella flexneri
<220> FEATURE:
<221> NAME/KEY: misc_feature
<222> LOCATION: (1)..(1017)
<223> OTHER INFORMATION: IpaH9.8 sequence encompassing catalytic domain
      (JRE 66)
<220> FEATURE:
<221> NAME/KEY: CDS
<222> LOCATION: (1)..(1017)

<400> SEQUENCE: 5 tca ata cat att agt gat aac cca tta tca tcc cat gct ctg caa gcc      48
Ser Ile His Ile Ser Asp Asn Pro Leu Ser Ser His Ala Leu Gln Ala
1               5                   10                  15 ctg caa aga tta acc tct tcg ccg gac tac cac ggc cca cgg att tac      96
Leu Gln Arg Leu Thr Ser Ser Pro Asp Tyr His Gly Pro Arg Ile Tyr
            20                  25                  30 ttc tcc atg agt gac gga caa cag aat aca ctc cat cgc ccc ctg gct    144
Phe Ser Met Ser Asp Gly Gln Gln Asn Thr Leu His Arg Pro Leu Ala
        35                  40                  45
```

| | |
|---|---|
| gat gcc gtg aca gca tgg ttc ccg gaa aac aaa caa tct gat gta tca<br>Asp Ala Val Thr Ala Trp Phe Pro Glu Asn Lys Gln Ser Asp Val Ser<br>50　　　　　　　　55　　　　　　　　60 | 192 |
| cag ata tgg cat gct ttt gaa cat gaa gag cat gcc aac acc ttt tcc<br>Gln Ile Trp His Ala Phe Glu His Glu Glu His Ala Asn Thr Phe Ser<br>65　　　　　　70　　　　　　　　75　　　　　　　　80 | 240 |
| gcg ttc ctt gac cgc ctt tcc gat acc gtc tct gca cgc aat acc tcc<br>Ala Phe Leu Asp Arg Leu Ser Asp Thr Val Ser Ala Arg Asn Thr Ser<br>　　　　　　85　　　　　　　　90　　　　　　　　95 | 288 |
| gga ttc cgt gaa cag gtc gct gca tgg ctg gaa aaa ctc agt gcc tct<br>Gly Phe Arg Glu Gln Val Ala Ala Trp Leu Glu Lys Leu Ser Ala Ser<br>100　　　　　　　　105　　　　　　　　110 | 336 |
| gcg gag ctt cga cag cag tct ttc gct gtt gct gct gat gcc act gag<br>Ala Glu Leu Arg Gln Gln Ser Phe Ala Val Ala Ala Asp Ala Thr Glu<br>115　　　　　　　　120　　　　　　　　125 | 384 |
| agc tgt gag gac cgt gtc gcg ctc aca tgg aac aat ctc cgg aaa acc<br>Ser Cys Glu Asp Arg Val Ala Leu Thr Trp Asn Asn Leu Arg Lys Thr<br>130　　　　　　　　135　　　　　　　　140 | 432 |
| ctc ctg gtc cat cag gca tca gaa ggc ctt ttc gat aat gat acc ggc<br>Leu Leu Val His Gln Ala Ser Glu Gly Leu Phe Asp Asn Asp Thr Gly<br>145　　　　　　　　150　　　　　　　　155　　　　　　　　160 | 480 |
| gct ctg ctc tcc ctg ggc agg gaa atg ttc cgc ctc gaa att ctg gag<br>Ala Leu Leu Ser Leu Gly Arg Glu Met Phe Arg Leu Glu Ile Leu Glu<br>　　　　　　165　　　　　　　　170　　　　　　　　175 | 528 |
| gat att gcc cgg gat aaa gtc aga act ctc cat ttt gtg gat gag ata<br>Asp Ile Ala Arg Asp Lys Val Arg Thr Leu His Phe Val Asp Glu Ile<br>180　　　　　　　　185　　　　　　　　190 | 576 |
| gaa gtc tac ctg gcc ttc cag acc atg ctc gca gag aaa ctt cag ctc<br>Glu Val Tyr Leu Ala Phe Gln Thr Met Leu Ala Glu Lys Leu Gln Leu<br>195　　　　　　　　200　　　　　　　　205 | 624 |
| tcc act gcc gtg aag gaa atg cgt ttc tat ggc gtg tcg gga gtg aca<br>Ser Thr Ala Val Lys Glu Met Arg Phe Tyr Gly Val Ser Gly Val Thr<br>210　　　　　　　　215　　　　　　　　220 | 672 |
| gca aat gac ctc cgc act gcc gaa gcc atg gtc aga agc cgt gaa gag<br>Ala Asn Asp Leu Arg Thr Ala Glu Ala Met Val Arg Ser Arg Glu Glu<br>225　　　　　　　　230　　　　　　　　235　　　　　　　　240 | 720 |
| aat gaa ttt acg gac tgg ttc tcc ctc tgg gga cca tgg cat gct gta<br>Asn Glu Phe Thr Asp Trp Phe Ser Leu Trp Gly Pro Trp His Ala Val<br>　　　　　　245　　　　　　　　250　　　　　　　　255 | 768 |
| ctg aag cgt acg gaa gct gac cgc tgg gcg cag gca gaa gag cag aaa<br>Leu Lys Arg Thr Glu Ala Asp Arg Trp Ala Gln Ala Glu Glu Gln Lys<br>260　　　　　　　　265　　　　　　　　270 | 816 |
| tat gag atg ctg gag aat gag tac cct cag agg gtg gct gac cgg ctg<br>Tyr Glu Met Leu Glu Asn Glu Tyr Pro Gln Arg Val Ala Asp Arg Leu<br>275　　　　　　　　280　　　　　　　　285 | 864 |
| aaa gca tca ggt ctg agc ggt gat gcg gat gcg gag agg gaa gcc ggt<br>Lys Ala Ser Gly Leu Ser Gly Asp Ala Asp Ala Glu Arg Glu Ala Gly<br>290　　　　　　　　295　　　　　　　　300 | 912 |
| gca cag gtg atg cgt gag act gaa cag cag att tac cgt cag ctg act<br>Ala Gln Val Met Arg Glu Thr Glu Gln Gln Ile Tyr Arg Gln Leu Thr<br>305　　　　　　　　310　　　　　　　　315　　　　　　　　320 | 960 |
| gac gag gta ctg gcc ctg cga ttg tct gaa aac ggc tca caa ctg cac<br>Asp Glu Val Leu Ala Leu Arg Leu Ser Glu Asn Gly Ser Gln Leu His<br>　　　　　　325　　　　　　　　330　　　　　　　　335 | 1008 |
| cat tca taa<br>His Ser | 1017 |

<210> SEQ ID NO 6
<211> LENGTH: 338

```
<212> TYPE: PRT
<213> ORGANISM: Shigella flexneri

<400> SEQUENCE: 6

Ser Ile His Ile Ser Asp Asn Pro Leu Ser His Ala Leu Gln Ala
1               5                   10                  15

Leu Gln Arg Leu Thr Ser Ser Pro Asp Tyr His Gly Pro Arg Ile Tyr
            20                  25                  30

Phe Ser Met Ser Asp Gly Gln Gln Asn Thr Leu His Arg Pro Leu Ala
        35                  40                  45

Asp Ala Val Thr Ala Trp Phe Pro Glu Asn Lys Gln Ser Asp Val Ser
    50                  55                  60

Gln Ile Trp His Ala Phe Glu His Glu His Ala Asn Thr Phe Ser
65                  70                  75                  80

Ala Phe Leu Asp Arg Leu Ser Asp Thr Val Ser Ala Arg Asn Thr Ser
                85                  90                  95

Gly Phe Arg Glu Gln Val Ala Ala Trp Leu Gly Lys Leu Ser Ala Ser
            100                 105                 110

Ala Glu Leu Arg Gln Gln Ser Phe Ala Val Ala Ala Asp Ala Thr Glu
        115                 120                 125

Ser Cys Glu Asp Arg Val Ala Leu Thr Trp Asn Asn Leu Arg Lys Thr
    130                 135                 140

Leu Leu Val His Gln Ala Ser Glu Gly Leu Phe Asp Asn Asp Thr Gly
145                 150                 155                 160

Ala Leu Leu Ser Leu Gly Arg Glu Met Phe Arg Leu Glu Ile Leu Glu
                165                 170                 175

Asp Ile Ala Arg Asp Lys Val Arg Thr Leu His Phe Val Asp Glu Ile
            180                 185                 190

Glu Val Tyr Leu Ala Phe Gln Thr Met Leu Ala Glu Lys Leu Gln Leu
        195                 200                 205

Ser Thr Ala Val Lys Glu Met Arg Phe Tyr Gly Val Ser Gly Val Thr
    210                 215                 220

Ala Asn Asp Leu Arg Thr Ala Glu Ala Met Val Arg Ser Arg Glu Glu
225                 230                 235                 240

Asn Glu Phe Thr Asp Trp Phe Ser Leu Trp Gly Pro Trp His Ala Val
                245                 250                 255

Leu Lys Arg Thr Glu Ala Asp Arg Trp Ala Gln Ala Glu Glu Gln Lys
            260                 265                 270

Tyr Glu Met Leu Glu Asn Glu Tyr Pro Gln Arg Val Ala Asp Arg Leu
        275                 280                 285

Lys Ala Ser Gly Leu Ser Gly Asp Ala Asp Ala Glu Arg Glu Ala Gly
    290                 295                 300

Ala Gln Val Met Arg Glu Thr Glu Gln Gln Ile Tyr Arg Gln Leu Thr
305                 310                 315                 320

Asp Glu Val Leu Ala Leu Arg Leu Ser Glu Asn Gly Ser Gln Leu His
                325                 330                 335

His Ser

<210> SEQ ID NO 7
<211> LENGTH: 1650
<212> TYPE: DNA
<213> ORGANISM: Salmonella typhimurium
<220> FEATURE:
<221> NAME/KEY: CDS
<222> LOCATION: (1)..(1650)
```

<400> SEQUENCE: 7

| | | | | | | | | | | | | | | | | |
|---|---|---|---|---|---|---|---|---|---|---|---|---|---|---|---|---|
| gaa | ttc | atg | tta | ccg | ata | aat | aat | aac | ttt | tca | ttg | ccc | caa | aat | tct | 48 |
| Glu | Phe | Met | Leu | Pro | Ile | Asn | Asn | Asn | Phe | Ser | Leu | Pro | Gln | Asn | Ser | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| ttt | tat | aac | act | att | tcc | ggt | aca | tat | gct | gat | tac | ttt | tca | gca | tgg | 96 |
| Phe | Tyr | Asn | Thr | Ile | Ser | Gly | Thr | Tyr | Ala | Asp | Tyr | Phe | Ser | Ala | Trp | |
| | | | 20 | | | | | 25 | | | | | 30 | | | |

| | | | | | | | | | | | | | | | | |
|---|---|---|---|---|---|---|---|---|---|---|---|---|---|---|---|---|
| gat | aaa | tgg | gaa | aaa | caa | gcg | ctc | ccc | ggt | gaa | gag | cgt | gat | gag | gct | 144 |
| Asp | Lys | Trp | Glu | Lys | Gln | Ala | Leu | Pro | Gly | Glu | Glu | Arg | Asp | Glu | Ala | |
| | | 35 | | | | | 40 | | | | | 45 | | | | |

| | | | | | | | | | | | | | | | | |
|---|---|---|---|---|---|---|---|---|---|---|---|---|---|---|---|---|
| gtc | tcc | cga | ctt | aaa | gaa | tgt | ctt | atc | aat | aat | tcc | gat | gaa | ctt | cga | 192 |
| Val | Ser | Arg | Leu | Lys | Glu | Cys | Leu | Ile | Asn | Asn | Ser | Asp | Glu | Leu | Arg | |
| 50 | | | | | 55 | | | | | 60 | | | | | | |

| | | | | | | | | | | | | | | | | |
|---|---|---|---|---|---|---|---|---|---|---|---|---|---|---|---|---|
| ctg | gac | cgt | tta | aat | ctg | tcc | tcg | cta | cct | gac | aac | tta | cca | gct | cag | 240 |
| Leu | Asp | Arg | Leu | Asn | Leu | Ser | Ser | Leu | Pro | Asp | Asn | Leu | Pro | Ala | Gln | |
| 65 | | | | 70 | | | | | 75 | | | | | 80 | | |

| | | | | | | | | | | | | | | | | |
|---|---|---|---|---|---|---|---|---|---|---|---|---|---|---|---|---|
| ata | acg | ctg | ctc | aat | gta | tca | tat | aat | caa | tta | act | aac | cta | cct | gaa | 288 |
| Ile | Thr | Leu | Leu | Asn | Val | Ser | Tyr | Asn | Gln | Leu | Thr | Asn | Leu | Pro | Glu | |
| | | | | 85 | | | | | 90 | | | | | 95 | | |

| | | | | | | | | | | | | | | | | |
|---|---|---|---|---|---|---|---|---|---|---|---|---|---|---|---|---|
| ctg | cct | gtt | acg | cta | aaa | aaa | tta | tat | tcc | gcc | agc | aat | aaa | tta | tca | 336 |
| Leu | Pro | Val | Thr | Leu | Lys | Lys | Leu | Tyr | Ser | Ala | Ser | Asn | Lys | Leu | Ser | |
| | | | 100 | | | | | 105 | | | | | 110 | | | |

| | | | | | | | | | | | | | | | | |
|---|---|---|---|---|---|---|---|---|---|---|---|---|---|---|---|---|
| gaa | ttg | ccc | gtg | cta | cct | cct | gcg | ctg | gag | tca | ctt | cag | gta | caa | cac | 384 |
| Glu | Leu | Pro | Val | Leu | Pro | Pro | Ala | Leu | Glu | Ser | Leu | Gln | Val | Gln | His | |
| | | 115 | | | | | 120 | | | | | 125 | | | | |

| | | | | | | | | | | | | | | | | |
|---|---|---|---|---|---|---|---|---|---|---|---|---|---|---|---|---|
| aat | gag | ctg | gaa | aac | ctg | cca | gct | tta | ccc | gat | tcg | tta | ttg | act | atg | 432 |
| Asn | Glu | Leu | Glu | Asn | Leu | Pro | Ala | Leu | Pro | Asp | Ser | Leu | Leu | Thr | Met | |
| | 130 | | | | | 135 | | | | | 140 | | | | | |

| | | | | | | | | | | | | | | | | |
|---|---|---|---|---|---|---|---|---|---|---|---|---|---|---|---|---|
| aat | atc | agc | tat | aac | gaa | ata | gtc | tcc | tta | cca | tcg | ctc | cca | cag | gct | 480 |
| Asn | Ile | Ser | Tyr | Asn | Glu | Ile | Val | Ser | Leu | Pro | Ser | Leu | Pro | Gln | Ala | |
| 145 | | | | | 150 | | | | | 155 | | | | | 160 | |

| | | | | | | | | | | | | | | | | |
|---|---|---|---|---|---|---|---|---|---|---|---|---|---|---|---|---|
| ctt | aaa | aat | ctc | aga | gcg | acc | cgt | aat | ttc | ctc | act | gag | cta | cca | gca | 528 |
| Leu | Lys | Asn | Leu | Arg | Ala | Thr | Arg | Asn | Phe | Leu | Thr | Glu | Leu | Pro | Ala | |
| | | | | 165 | | | | | 170 | | | | | 175 | | |

| | | | | | | | | | | | | | | | | |
|---|---|---|---|---|---|---|---|---|---|---|---|---|---|---|---|---|
| ttt | tct | gag | gga | aat | aat | ccc | gtt | gtc | aga | gag | tat | ttt | ttt | gat | aga | 576 |
| Phe | Ser | Glu | Gly | Asn | Asn | Pro | Val | Val | Arg | Glu | Tyr | Phe | Phe | Asp | Arg | |
| | | | 180 | | | | | 185 | | | | | 190 | | | |

| | | | | | | | | | | | | | | | | |
|---|---|---|---|---|---|---|---|---|---|---|---|---|---|---|---|---|
| aat | cag | ata | agt | cat | atc | ccg | gaa | agc | att | ctt | aat | ctg | agg | aat | gaa | 624 |
| Asn | Gln | Ile | Ser | His | Ile | Pro | Glu | Ser | Ile | Leu | Asn | Leu | Arg | Asn | Glu | |
| | | 195 | | | | | 200 | | | | | 205 | | | | |

| | | | | | | | | | | | | | | | | |
|---|---|---|---|---|---|---|---|---|---|---|---|---|---|---|---|---|
| tgt | tca | ata | cat | att | agt | gat | aac | cca | tta | tca | tcc | cat | gct | ctg | caa | 672 |
| Cys | Ser | Ile | His | Ile | Ser | Asp | Asn | Pro | Leu | Ser | Ser | His | Ala | Leu | Gln | |
| | 210 | | | | | 215 | | | | | 220 | | | | | |

| | | | | | | | | | | | | | | | | |
|---|---|---|---|---|---|---|---|---|---|---|---|---|---|---|---|---|
| gcc | ctg | caa | aga | tta | acc | tct | tcg | ccg | gac | tac | cac | ggc | cca | cgg | att | 720 |
| Ala | Leu | Gln | Arg | Leu | Thr | Ser | Ser | Pro | Asp | Tyr | His | Gly | Pro | Arg | Ile | |
| 225 | | | | | 230 | | | | | 235 | | | | | 240 | |

| | | | | | | | | | | | | | | | | |
|---|---|---|---|---|---|---|---|---|---|---|---|---|---|---|---|---|
| tac | ttc | tcc | atg | agt | gac | gga | caa | cag | aat | aca | ctc | cat | cgc | ccc | ctg | 768 |
| Tyr | Phe | Ser | Met | Ser | Asp | Gly | Gln | Gln | Asn | Thr | Leu | His | Arg | Pro | Leu | |
| | | | | 245 | | | | | 250 | | | | | 255 | | |

| | | | | | | | | | | | | | | | | |
|---|---|---|---|---|---|---|---|---|---|---|---|---|---|---|---|---|
| gct | gat | gcc | gtg | aca | gca | tgg | ttc | ccg | gaa | aac | aaa | caa | tct | gat | gta | 816 |
| Ala | Asp | Ala | Val | Thr | Ala | Trp | Phe | Pro | Glu | Asn | Lys | Gln | Ser | Asp | Val | |
| | | | 260 | | | | | 265 | | | | | 270 | | | |

| | | | | | | | | | | | | | | | | |
|---|---|---|---|---|---|---|---|---|---|---|---|---|---|---|---|---|
| tca | cag | ata | tgg | cat | gct | ttt | gaa | cat | gaa | gag | cat | gcc | aac | acc | ttt | 864 |
| Ser | Gln | Ile | Trp | His | Ala | Phe | Glu | His | Glu | Glu | His | Ala | Asn | Thr | Phe | |
| | | 275 | | | | | 280 | | | | | 285 | | | | |

| | | | | | | | | | | | | | | | | |
|---|---|---|---|---|---|---|---|---|---|---|---|---|---|---|---|---|
| tcc | gcg | ttc | ctt | gac | cgc | ctt | tcc | gat | acc | gtc | tct | gca | cgc | aat | acc | 912 |
| Ser | Ala | Phe | Leu | Asp | Arg | Leu | Ser | Asp | Thr | Val | Ser | Ala | Arg | Asn | Thr | |
| | 290 | | | | | 295 | | | | | 300 | | | | | |

| | | | | | | | | | | | | | | | | |
|---|---|---|---|---|---|---|---|---|---|---|---|---|---|---|---|---|
| tcc | gga | ttc | cgt | gaa | cag | gtc | gct | gca | tgg | ctg | gaa | aaa | ctc | agt | gcc | 960 |

```
Ser Gly Phe Arg Glu Gln Val Ala Ala Trp Leu Glu Lys Leu Ser Ala
305                 310                 315                 320 tct gcg gag ctt cga cag cag tct ttc gct gtt gct gct gat gcc act     1008
Ser Ala Glu Leu Arg Gln Gln Ser Phe Ala Val Ala Ala Asp Ala Thr
                325                 330                 335 gag agc tgt gag gac cgt gtc gcg ctc aca tgg aac aat ctc cgg aaa     1056
Glu Ser Cys Glu Asp Arg Val Ala Leu Thr Trp Asn Asn Leu Arg Lys
            340                 345                 350 acc ctc ctg gtc cat cag gca tca gaa ggc ctt ttc gat aat gat acc     1104
Thr Leu Leu Val His Gln Ala Ser Glu Gly Leu Phe Asp Asn Asp Thr
        355                 360                 365 ggc gct ctg ctc tcc ctg ggc agg gaa atg ttc cgc ctc gaa att ctg     1152
Gly Ala Leu Leu Ser Leu Gly Arg Glu Met Phe Arg Leu Glu Ile Leu
    370                 375                 380 gag gat att gcc cgg gat aaa gtc aga act ctc cat ttt gtg gat gag     1200
Glu Asp Ile Ala Arg Asp Lys Val Arg Thr Leu His Phe Val Asp Glu
385                 390                 395                 400 ata gaa gtc tac ctg gcc ttc cag acc atg ctc gca gag aaa ctt cag     1248
Ile Glu Val Tyr Leu Ala Phe Gln Thr Met Leu Ala Glu Lys Leu Gln
                405                 410                 415 ctc tcc act gcc gtg aag gaa atg cgt ttc tat ggc gtg tcg gga gtg     1296
Leu Ser Thr Ala Val Lys Glu Met Arg Phe Tyr Gly Val Ser Gly Val
            420                 425                 430 aca gca aat gac ctc cgc act gcc gaa gcc atg gtc aga agc cgt gaa     1344
Thr Ala Asn Asp Leu Arg Thr Ala Glu Ala Met Val Arg Ser Arg Glu
        435                 440                 445 gag aat gaa ttt acg gac tgg ttc tcc ctc tgg gga cca tgg cat gct     1392
Glu Asn Glu Phe Thr Asp Trp Phe Ser Leu Trp Gly Pro Trp His Ala
    450                 455                 460 gta ctg aag cgt acg gaa gct gac cgc tgg gcg cag gca gaa gag cag     1440
Val Leu Lys Arg Thr Glu Ala Asp Arg Trp Ala Gln Ala Glu Glu Gln
465                 470                 475                 480 aaa tat gag atg ctg gag aat gag tac cct cag agg gtg gct gac cgg     1488
Lys Tyr Glu Met Leu Glu Asn Glu Tyr Pro Gln Arg Val Ala Asp Arg
                485                 490                 495 ctg aaa gca tca ggt ctg agc ggt gat gcg gat gcg gag agg gaa gcc     1536
Leu Lys Ala Ser Gly Leu Ser Gly Asp Ala Asp Ala Glu Arg Glu Ala
            500                 505                 510 ggt gca cag gtg atg cgt gag act gaa cag cag att tac cgt cag ctg     1584
Gly Ala Gln Val Met Arg Glu Thr Glu Gln Gln Ile Tyr Arg Gln Leu
        515                 520                 525 act gac gag gta ctg gcc ctg cga ttg ttt gaa aac ggc tca caa ctg     1632
Thr Asp Glu Val Leu Ala Leu Arg Leu Phe Glu Asn Gly Ser Gln Leu
    530                 535                 540 cac cat tca taa aag ctt                                             1650
His His Ser     Lys Leu
545

<210> SEQ ID NO 8
<211> LENGTH: 547
<212> TYPE: PRT
<213> ORGANISM: Salmonella typhimurium

<400> SEQUENCE: 8

Glu Phe Met Leu Pro Ile Asn Asn Phe Ser Leu Pro Gln Asn Ser
1               5                   10                  15

Phe Tyr Asn Thr Ile Ser Gly Thr Tyr Ala Asp Tyr Phe Ser Ala Trp
            20                  25                  30

Asp Lys Trp Glu Lys Gln Ala Leu Pro Gly Glu Glu Arg Asp Glu Ala
        35                  40                  45
```

```
Val Ser Arg Leu Lys Glu Cys Leu Ile Asn Asn Ser Asp Glu Leu Arg
 50                  55                  60

Leu Asp Arg Leu Asn Leu Ser Ser Leu Pro Asp Asn Leu Pro Ala Gln
 65                  70                  75                  80

Ile Thr Leu Leu Asn Val Ser Tyr Asn Gln Leu Thr Asn Leu Pro Glu
                 85                  90                  95

Leu Pro Val Thr Leu Lys Lys Leu Tyr Ser Ala Ser Asn Lys Leu Ser
            100                 105                 110

Glu Leu Pro Val Leu Pro Pro Ala Leu Glu Ser Leu Gln Val Gln His
            115                 120                 125

Asn Glu Leu Glu Asn Leu Pro Ala Leu Pro Asp Ser Leu Leu Thr Met
130                 135                 140

Asn Ile Ser Tyr Asn Glu Ile Val Ser Leu Pro Ser Leu Pro Gln Ala
145                 150                 155                 160

Leu Lys Asn Leu Arg Ala Thr Arg Asn Phe Leu Thr Glu Leu Pro Ala
                165                 170                 175

Phe Ser Glu Gly Asn Asn Pro Val Val Arg Glu Tyr Phe Phe Asp Arg
            180                 185                 190

Asn Gln Ile Ser His Ile Pro Glu Ser Ile Leu Asn Leu Arg Asn Glu
            195                 200                 205

Cys Ser Ile His Ile Ser Asp Asn Pro Leu Ser Ser His Ala Leu Gln
210                 215                 220

Ala Leu Gln Arg Leu Thr Ser Ser Pro Asp Tyr His Gly Pro Arg Ile
225                 230                 235                 240

Tyr Phe Ser Met Ser Asp Gly Gln Gln Asn Thr Leu His Arg Pro Leu
                245                 250                 255

Ala Asp Ala Val Thr Ala Trp Phe Pro Glu Asn Lys Gln Ser Asp Val
            260                 265                 270

Ser Gln Ile Trp His Ala Phe Glu His Glu Glu His Ala Asn Thr Phe
            275                 280                 285

Ser Ala Phe Leu Asp Arg Leu Ser Asp Thr Val Ser Ala Arg Asn Thr
290                 295                 300

Ser Gly Phe Arg Glu Gln Val Ala Ala Trp Leu Glu Lys Leu Ser Ala
305                 310                 315                 320

Ser Ala Glu Leu Arg Gln Gln Ser Phe Ala Val Ala Asp Ala Thr
                325                 330                 335

Glu Ser Cys Glu Asp Arg Val Ala Leu Thr Trp Asn Asn Leu Arg Lys
            340                 345                 350

Thr Leu Leu Val His Gln Ala Ser Glu Gly Leu Phe Asp Asn Asp Thr
                355                 360                 365

Gly Ala Leu Leu Ser Leu Gly Arg Glu Met Phe Arg Leu Glu Ile Leu
            370                 375                 380

Glu Asp Ile Ala Arg Asp Lys Val Arg Thr Leu His Phe Val Asp Glu
385                 390                 395                 400

Ile Glu Val Tyr Leu Ala Phe Gln Thr Met Leu Ala Glu Lys Leu Gln
                405                 410                 415

Leu Ser Thr Ala Val Lys Glu Met Arg Phe Tyr Gly Val Ser Gly Val
            420                 425                 430

Thr Ala Asn Asp Leu Arg Thr Ala Glu Ala Met Val Arg Ser Arg Glu
            435                 440                 445

Glu Asn Glu Phe Thr Asp Trp Phe Ser Leu Trp Gly Pro Trp His Ala
450                 455                 460
```

```
Val Leu Lys Arg Thr Glu Ala Asp Arg Trp Ala Gln Ala Glu Glu Gln
465                 470                 475                 480

Lys Tyr Glu Met Leu Glu Asn Glu Tyr Pro Gln Arg Val Ala Asp Arg
                485                 490                 495

Leu Lys Ala Ser Gly Leu Ser Gly Asp Ala Asp Ala Glu Arg Glu Ala
            500                 505                 510

Gly Ala Gln Val Met Arg Glu Thr Glu Gln Gln Ile Tyr Arg Gln Leu
        515                 520                 525

Thr Asp Glu Val Leu Ala Leu Arg Leu Phe Glu Asn Gly Ser Gln Leu
    530                 535                 540

His His Ser
545

<210> SEQ ID NO 9
<211> LENGTH: 1023
<212> TYPE: DNA
<213> ORGANISM: Salmonella typhimurium
<220> FEATURE:
<221> NAME/KEY: CDS
<222> LOCATION: (1)..(1014)
<220> FEATURE:
<221> NAME/KEY: misc_feature
<222> LOCATION: (1)..(1014)
<223> OTHER INFORMATION: Nucleotides 1081 to 2103 of sspH1 gene encoding
      catalytic domain

<400> SEQUENCE: 9
```

| | | | | | | | | | | | | | | | | |
|---|---|---|---|---|---|---|---|---|---|---|---|---|---|---|---|---|
| tca | gcg | gca | cgc | gta | tat | ctg | gac | ggg | aat | cca | ctg | tct | gta | cgc | act | 48 |
| Ser | Ala | Ala | Arg | Val | Tyr | Leu | Asp | Gly | Asn | Pro | Leu | Ser | Val | Arg | Thr | |
| 1 | | | | 5 | | | | | 10 | | | | | 15 | | |
| ctg | cag | gct | ctg | cgg | gac | atc | att | ggc | cat | tca | ggc | atc | agg | ata | cac | 96 |
| Leu | Gln | Ala | Leu | Arg | Asp | Ile | Ile | Gly | His | Ser | Gly | Ile | Arg | Ile | His | |
| | | 20 | | | | | 25 | | | | | 30 | | | | |
| ttc | gat | atg | gcg | ggg | cct | tcc | gtc | ccc | cgg | gaa | gcc | cgg | gca | ctg | cac | 144 |
| Phe | Asp | Met | Ala | Gly | Pro | Ser | Val | Pro | Arg | Glu | Ala | Arg | Ala | Leu | His | |
| | | | 35 | | | | | 40 | | | | | 45 | | | |
| ctg | gcg | gtc | gct | gac | tgg | ctg | acg | tct | gca | cgg | gag | ggg | gaa | gcg | gcc | 192 |
| Leu | Ala | Val | Ala | Asp | Trp | Leu | Thr | Ser | Ala | Arg | Glu | Gly | Glu | Ala | Ala | |
| | 50 | | | | | 55 | | | | | 60 | | | | | |
| cag | gca | gac | aga | tgg | cag | gcg | ttc | gga | ctg | gaa | gat | aac | gcc | gcc | gcc | 240 |
| Gln | Ala | Asp | Arg | Trp | Gln | Ala | Phe | Gly | Leu | Glu | Asp | Asn | Ala | Ala | Ala | |
| 65 | | | | | 70 | | | | | 75 | | | | | 80 | |
| ttc | agc | ctg | gtc | ctg | gac | aga | ctg | cgt | gag | acg | gaa | aac | ttc | aaa | aaa | 288 |
| Phe | Ser | Leu | Val | Leu | Asp | Arg | Leu | Arg | Glu | Thr | Glu | Asn | Phe | Lys | Lys | |
| | | | | 85 | | | | | 90 | | | | | 95 | | |
| gac | gcg | ggc | ttt | aag | gca | cag | ata | tca | tcc | tgg | ctg | aca | caa | ctg | gct | 336 |
| Asp | Ala | Gly | Phe | Lys | Ala | Gln | Ile | Ser | Ser | Trp | Leu | Thr | Gln | Leu | Ala | |
| | | | 100 | | | | | 105 | | | | | 110 | | | |
| gaa | gat | gct | gcg | ctg | aga | gca | aaa | acc | ttt | gcc | atg | gca | aca | gag | gca | 384 |
| Glu | Asp | Ala | Ala | Leu | Arg | Ala | Lys | Thr | Phe | Ala | Met | Ala | Thr | Glu | Ala | |
| | | | | 115 | | | | | 120 | | | | | 125 | | |
| aca | tca | acc | tgc | gag | gac | cgg | gtc | aca | cat | gcc | ctg | cac | cag | atg | aat | 432 |
| Thr | Ser | Thr | Cys | Glu | Asp | Arg | Val | Thr | His | Ala | Leu | His | Gln | Met | Asn | |
| | 130 | | | | | 135 | | | | | 140 | | | | | |
| aac | gta | caa | ctg | gta | cat | aat | gca | gaa | aaa | ggg | gaa | tac | gac | aac | aat | 480 |
| Asn | Val | Gln | Leu | Val | His | Asn | Ala | Glu | Lys | Gly | Glu | Tyr | Asp | Asn | Asn | |
| 145 | | | | | 150 | | | | | 155 | | | | | 160 | |
| ctc | cag | ggg | ctg | gtt | tcc | acg | ggg | cgt | gag | atg | ttc | cgc | ctg | gca | aca | 528 |
| Leu | Gln | Gly | Leu | Val | Ser | Thr | Gly | Arg | Glu | Met | Phe | Arg | Leu | Ala | Thr | |
| | | | | 165 | | | | | 170 | | | | | 175 | | |
| ctg | gaa | cag | att | gcc | cgg | gaa | aaa | gcc | gga | aca | ctg | gct | tta | gtc | gat | 576 |

```
Leu Glu Gln Ile Ala Arg Glu Lys Ala Gly Thr Leu Ala Leu Val Asp
            180                 185                 190 gac gtt gag gtc tat ctg gcg ttc cag aat aag ctg aag gaa tca ctt        624
Asp Val Glu Val Tyr Leu Ala Phe Gln Asn Lys Leu Lys Glu Ser Leu
        195                 200                 205 gag ctg acc agc gtg acg tca gaa atg cgt ttc ttt gac gtt tcc ggc        672
Glu Leu Thr Ser Val Thr Ser Glu Met Arg Phe Phe Asp Val Ser Gly
    210                 215                 220 gtg acg gtt tca gac ctt cag gct gcg gag ctt cag gtg aaa acc gct        720
Val Thr Val Ser Asp Leu Gln Ala Ala Glu Leu Gln Val Lys Thr Ala
225                 230                 235                 240 gaa aac agc ggg ttc agt aaa tgg ata ctg cag tgg ggg ccg tta cac        768
Glu Asn Ser Gly Phe Ser Lys Trp Ile Leu Gln Trp Gly Pro Leu His
                245                 250                 255 agc gtg ctg gaa cgc aaa gtg ccg gaa cgc ttt aac gcg ctt cgt gaa        816
Ser Val Leu Glu Arg Lys Val Pro Glu Arg Phe Asn Ala Leu Arg Glu
            260                 265                 270 aag caa ata tcg gat tat gaa gac acg tac cgg aag ctg tat gac gaa        864
Lys Gln Ile Ser Asp Tyr Glu Asp Thr Tyr Arg Lys Leu Tyr Asp Glu
        275                 280                 285 gtg ctg aaa tcg tcc ggg ctg gtc gac gat acc gat gca gaa cgt act        912
Val Leu Lys Ser Ser Gly Leu Val Asp Asp Thr Asp Ala Glu Arg Thr
    290                 295                 300 atc gga gta agt gcg atg gat agt gcg aaa aaa gaa ttt ctg gat ggc        960
Ile Gly Val Ser Ala Met Asp Ser Ala Lys Lys Glu Phe Leu Asp Gly
305                 310                 315                 320 ctg cgc gct ctt gtg gat gag gtg ctg ggt agc tat ctg aca gcc cgg       1008
Leu Arg Ala Leu Val Asp Glu Val Leu Gly Ser Tyr Leu Thr Ala Arg
                325                 330                 335 tgg cgt cttaactga                                                      1023
Trp Arg <210> SEQ ID NO 10
<211> LENGTH: 338
<212> TYPE: PRT
<213> ORGANISM: Salmonella typhimurium

<400> SEQUENCE: 10

Ser Ala Ala Arg Val Tyr Leu Asp Gly Asn Pro Leu Ser Val Arg Thr
1               5                   10                  15

Leu Gln Ala Leu Arg Asp Ile Ile Gly His Ser Gly Ile Arg Ile His
            20                  25                  30

Phe Asp Met Ala Gly Pro Ser Val Pro Arg Glu Ala Arg Ala Leu His
        35                  40                  45

Leu Ala Val Ala Asp Trp Leu Thr Ser Ala Arg Glu Gly Glu Ala Ala
    50                  55                  60

Gln Ala Asp Arg Trp Gln Ala Phe Gly Leu Glu Asp Asn Ala Ala Ala
65                  70                  75                  80

Phe Ser Leu Val Leu Asp Arg Leu Arg Glu Thr Asn Phe Lys Lys
            85                  90                  95

Asp Ala Gly Phe Lys Ala Gln Ile Ser Ser Trp Leu Thr Gln Leu Ala
        100                 105                 110

Glu Asp Ala Ala Leu Arg Ala Lys Thr Phe Ala Met Ala Thr Glu Ala
    115                 120                 125

Thr Ser Thr Cys Glu Asp Arg Val Thr His Ala Leu His Gln Met Asn
130                 135                 140

Asn Val Gln Leu Val His Asn Ala Glu Lys Gly Glu Tyr Asp Asn Asn
145                 150                 155                 160
```

-continued

```
Leu Gln Gly Leu Val Ser Thr Gly Arg Glu Met Phe Arg Leu Ala Thr
                165                 170                 175
Leu Glu Gln Ile Ala Arg Glu Lys Ala Gly Thr Leu Ala Leu Val Asp
            180                 185                 190
Asp Val Glu Val Tyr Leu Ala Phe Gln Asn Lys Leu Lys Glu Ser Leu
        195                 200                 205
Glu Leu Thr Ser Val Thr Ser Glu Met Arg Phe Phe Asp Val Ser Gly
    210                 215                 220
Val Thr Val Ser Asp Leu Gln Ala Ala Glu Leu Gln Val Lys Thr Ala
225                 230                 235                 240
Glu Asn Ser Gly Phe Ser Lys Trp Ile Leu Gln Trp Gly Pro Leu His
                245                 250                 255
Ser Val Leu Glu Arg Lys Val Pro Glu Arg Phe Asn Ala Leu Arg Glu
            260                 265                 270
Lys Gln Ile Ser Asp Tyr Glu Asp Thr Tyr Arg Lys Leu Tyr Asp Glu
        275                 280                 285
Val Leu Lys Ser Ser Gly Leu Val Asp Asp Thr Asp Ala Glu Arg Thr
    290                 295                 300
Ile Gly Val Ser Ala Met Asp Ser Ala Lys Lys Glu Phe Leu Asp Gly
305                 310                 315                 320
Leu Arg Ala Leu Val Asp Glu Val Leu Gly Ser Tyr Leu Thr Ala Arg
                325                 330                 335
Trp Arg
```

<210> SEQ ID NO 11
<211> LENGTH: 1650
<212> TYPE: DNA
<213> ORGANISM: Shigella flexneri
<220> FEATURE:
<221> NAME/KEY: misc_feature
<222> LOCATION: (1)..(1650)
<223> OTHER INFORMATION: JRE 52 insert
<220> FEATURE:
<221> NAME/KEY: CDS
<222> LOCATION: (7)..(1641)

<400> SEQUENCE: 11

```
ggatct atg tta ccg ata aat aat aac ttt tca ttg ccc caa aat tct         48
       Met Leu Pro Ile Asn Asn Asn Phe Ser Leu Pro Gln Asn Ser
         1               5                  10 ttt tat aac act att tcc ggt aca tat gct gat tac ttt tca gca tgg       96
Phe Tyr Asn Thr Ile Ser Gly Thr Tyr Ala Asp Tyr Phe Ser Ala Trp
 15                  20                  25                  30 gat aaa tgg gaa aaa caa gcg ctc ccc ggt gaa gag cgt gat gag gct      144
Asp Lys Trp Glu Lys Gln Ala Leu Pro Gly Glu Glu Arg Asp Glu Ala
                 35                  40                  45 gtc tcc cga ctt aaa gaa tgt ctt atc aat aat tcc gat gaa ctt cga      192
Val Ser Arg Leu Lys Glu Cys Leu Ile Asn Asn Ser Asp Glu Leu Arg
             50                  55                  60 ctg gac cgt tta aat ctg tcc tcg cta cct gac aac tta cca gct cag      240
Leu Asp Arg Leu Asn Leu Ser Ser Leu Pro Asp Asn Leu Pro Ala Gln
         65                  70                  75 ata acg ctg ctc aat gta tca tat aat caa tta act aac cta cct gaa      288
Ile Thr Leu Leu Asn Val Ser Tyr Asn Gln Leu Thr Asn Leu Pro Glu
     80                  85                  90 ctg cct gtt acg cta aaa aaa tta tat tcc gcc agc aat aaa tta tca      336
Leu Pro Val Thr Leu Lys Lys Leu Tyr Ser Ala Ser Asn Lys Leu Ser
 95                 100                 105                 110
```

```
gaa ttg ccc gtg cta cct cct gcg ctg gag tca ctt cag gta caa cac         384
Glu Leu Pro Val Leu Pro Pro Ala Leu Glu Ser Leu Gln Val Gln His
            115                 120                 125 aat gag ctg gaa aac ctg cca gct tta ccc gat tcg tta ttg act atg         432
Asn Glu Leu Glu Asn Leu Pro Ala Leu Pro Asp Ser Leu Leu Thr Met
            130                 135                 140 aat atc agc tat aac gaa ata gtc tcc tta cca tcg ctc cca cag gct         480
Asn Ile Ser Tyr Asn Glu Ile Val Ser Leu Pro Ser Leu Pro Gln Ala
            145                 150                 155 ctt aaa aat ctc aga gcg acc cgt aat ttc ctc act gag cta cca gca         528
Leu Lys Asn Leu Arg Ala Thr Arg Asn Phe Leu Thr Glu Leu Pro Ala
    160                 165                 170 ttt tct gag gga aat aat ccc gtt gtc aga gag tat ttt ttt gat aga         576
Phe Ser Glu Gly Asn Asn Pro Val Val Arg Glu Tyr Phe Phe Asp Arg
175                 180                 185                 190 aat cag ata agt cat atc ccg gaa agc att ctt aat ctg agg aat gaa         624
Asn Gln Ile Ser His Ile Pro Glu Ser Ile Leu Asn Leu Arg Asn Glu
                195                 200                 205 tgt tca ata cat att agt gat aac cca tta tca tcc cat gct ctg caa         672
Cys Ser Ile His Ile Ser Asp Asn Pro Leu Ser Ser His Ala Leu Gln
            210                 215                 220 gcc ctg caa aga tta acc tct tcg ccg gac tac cac ggc cca cgg att         720
Ala Leu Gln Arg Leu Thr Ser Ser Pro Asp Tyr His Gly Pro Arg Ile
            225                 230                 235 tac ttc tcc atg agt gac gga caa cag aat aca ctc cat cgc ccc ctg         768
Tyr Phe Ser Met Ser Asp Gly Gln Gln Asn Thr Leu His Arg Pro Leu
            240                 245                 250 gct gat gcc gtg aca gca tgg ttc ccg gaa aac aaa caa tct gat gta         816
Ala Asp Ala Val Thr Ala Trp Phe Pro Glu Asn Lys Gln Ser Asp Val
255                 260                 265                 270 tca cag ata tgg cat gct ttt gaa cat gaa gag cat gcc aac acc ttt         864
Ser Gln Ile Trp His Ala Phe Glu His Glu Glu His Ala Asn Thr Phe
                275                 280                 285 tcc gcg ttc ctt gac cgc ctt tcc gat acc gtc tct gca cgc aat acc         912
Ser Ala Phe Leu Asp Arg Leu Ser Asp Thr Val Ser Ala Arg Asn Thr
            290                 295                 300 tcc gga ttc cgt gaa cag gtc gct gca tgg ctg gaa aaa ctc agt gcc         960
Ser Gly Phe Arg Glu Gln Val Ala Ala Trp Leu Glu Lys Leu Ser Ala
            305                 310                 315 tct gcg gag ctt cga cag cag tct ttc gct gtt gct gct gat gcc act        1008
Ser Ala Glu Leu Arg Gln Gln Ser Phe Ala Val Ala Ala Asp Ala Thr
            320                 325                 330 gag agc tgt gag gac cgt gtc gcg ctc aca tgg aac aat ctc cgg aaa        1056
Glu Ser Cys Glu Asp Arg Val Ala Leu Thr Trp Asn Asn Leu Arg Lys
335                 340                 345                 350 acc ctc ctg gtc cat cag gca tca gaa ggc ctt ttc gat aat gat acc        1104
Thr Leu Leu Val His Gln Ala Ser Glu Gly Leu Phe Asp Asn Asp Thr
                355                 360                 365 ggc gct ctg ctc tcc ctg ggc agg gaa atg ttc cgc ctc gaa att ctg        1152
Gly Ala Leu Leu Ser Leu Gly Arg Glu Met Phe Arg Leu Glu Ile Leu
            370                 375                 380 gag gat att gcc cgg gat aaa gtc aga act ctc cat ttt gtg gat gag        1200
Glu Asp Ile Ala Arg Asp Lys Val Arg Thr Leu His Phe Val Asp Glu
            385                 390                 395 ata gaa gtc tac ctg gcc ttc cag acc atg ctc gca gag aaa ctt cag        1248
Ile Glu Val Tyr Leu Ala Phe Gln Thr Met Leu Ala Glu Lys Leu Gln
            400                 405                 410 ctc tcc act gcc gtg aag gaa atg cgt ttc tat ggc gtg tcg gga gtg        1296
Leu Ser Thr Ala Val Lys Glu Met Arg Phe Tyr Gly Val Ser Gly Val
415                 420                 425                 430
```

```
aca gca aat gac ctc cgc act gcc gaa gcc atg gtc aga agc cgt gaa    1344
Thr Ala Asn Asp Leu Arg Thr Ala Glu Ala Met Val Arg Ser Arg Glu
                435                 440                 445 gag aat gaa ttt acg gac tgg ttc tcc ctc tgg gga cca tgg cat gct    1392
Glu Asn Glu Phe Thr Asp Trp Phe Ser Leu Trp Gly Pro Trp His Ala
            450                 455                 460 gta ctg aag cgt acg gaa gct gac cgc tgg gcg cag gca gaa gag cag    1440
Val Leu Lys Arg Thr Glu Ala Asp Arg Trp Ala Gln Ala Glu Glu Gln
        465                 470                 475 aaa tat gag atg ctg gag aat gag tac cct cag agg gtg gct gac cgg    1488
Lys Tyr Glu Met Leu Glu Asn Glu Tyr Pro Gln Arg Val Ala Asp Arg
    480                 485                 490 ctg aaa gca tca ggt ctg agc ggt gat gcg gat gcg gag agg gaa gcc    1536
Leu Lys Ala Ser Gly Leu Ser Gly Asp Ala Asp Ala Glu Arg Glu Ala
495                 500                 505                 510 ggt gca cag gtg atg cgt gag act gaa cag cag att tac cgt cag ctg    1584
Gly Ala Gln Val Met Arg Glu Thr Glu Gln Gln Ile Tyr Arg Gln Leu
                515                 520                 525 act gac gag gta ctg gcc ctg cga ttg ttt gaa aac ggc tca caa ctg    1632
Thr Asp Glu Val Leu Ala Leu Arg Leu Phe Glu Asn Gly Ser Gln Leu
            530                 535                 540 cac cat tca taactcgag                                              1650
His His Ser
        545

<210> SEQ ID NO 12
<211> LENGTH: 545
<212> TYPE: PRT
<213> ORGANISM: Shigella flexneri

<400> SEQUENCE: 12

Met Leu Pro Ile Asn Asn Phe Ser Leu Pro Gln Asn Ser Phe Tyr
1               5                   10                  15

Asn Thr Ile Ser Gly Thr Tyr Ala Asp Tyr Phe Ser Ala Trp Asp Lys
            20                  25                  30

Trp Glu Lys Gln Ala Leu Pro Gly Glu Glu Arg Asp Glu Ala Val Ser
        35                  40                  45

Arg Leu Lys Glu Cys Leu Ile Asn Asn Ser Asp Glu Leu Arg Leu Asp
    50                  55                  60

Arg Leu Asn Leu Ser Ser Leu Pro Asp Asn Leu Pro Ala Gln Ile Thr
65                  70                  75                  80

Leu Leu Asn Val Ser Tyr Asn Gln Leu Thr Asn Leu Pro Glu Leu Pro
                85                  90                  95

Val Thr Leu Lys Lys Leu Tyr Ser Ala Ser Asn Lys Leu Ser Glu Leu
            100                 105                 110

Pro Val Leu Pro Pro Ala Leu Glu Ser Leu Gln Val Gln His Asn Glu
        115                 120                 125

Leu Glu Asn Leu Pro Ala Leu Pro Asp Ser Leu Leu Thr Met Asn Ile
    130                 135                 140

Ser Tyr Asn Glu Ile Val Ser Leu Pro Ser Leu Pro Gln Ala Leu Lys
145                 150                 155                 160

Asn Leu Arg Ala Thr Arg Asn Phe Leu Thr Glu Leu Pro Ala Phe Ser
                165                 170                 175

Glu Gly Asn Asn Pro Val Val Arg Glu Tyr Phe Phe Asp Arg Asn Gln
            180                 185                 190

Ile Ser His Ile Pro Glu Ser Ile Leu Asn Leu Arg Asn Glu Cys Ser
        195                 200                 205
```

```
Ile His Ile Ser Asp Asn Pro Leu Ser Ser His Ala Leu Gln Ala Leu
        210                 215                 220

Gln Arg Leu Thr Ser Ser Pro Asp Tyr His Gly Pro Arg Ile Tyr Phe
225                 230                 235                 240

Ser Met Ser Asp Gly Gln Gln Asn Thr Leu His Arg Pro Leu Ala Asp
                245                 250                 255

Ala Val Thr Ala Trp Phe Pro Glu Asn Lys Gln Ser Asp Val Ser Gln
            260                 265                 270

Ile Trp His Ala Phe Glu His Glu His Ala Asn Thr Phe Ser Ala
                275                 280                 285

Phe Leu Asp Arg Leu Ser Asp Thr Val Ser Ala Arg Asn Thr Ser Gly
        290                 295                 300

Phe Arg Glu Gln Val Ala Ala Trp Leu Glu Lys Leu Ser Ala Ser Ala
305                 310                 315                 320

Glu Leu Arg Gln Gln Ser Phe Ala Val Ala Ala Asp Ala Thr Glu Ser
                325                 330                 335

Cys Glu Asp Arg Val Ala Leu Thr Trp Asn Asn Leu Arg Lys Thr Leu
            340                 345                 350

Leu Val His Gln Ala Ser Glu Gly Leu Phe Asp Asn Asp Thr Gly Ala
                355                 360                 365

Leu Leu Ser Leu Gly Arg Glu Met Phe Arg Leu Glu Ile Leu Glu Asp
        370                 375                 380

Ile Ala Arg Asp Lys Val Arg Thr Leu His Phe Val Asp Glu Ile Glu
385                 390                 395                 400

Val Tyr Leu Ala Phe Gln Thr Met Leu Ala Glu Lys Leu Gln Leu Ser
                405                 410                 415

Thr Ala Val Lys Glu Met Arg Phe Tyr Gly Val Ser Gly Val Thr Ala
            420                 425                 430

Asn Asp Leu Arg Thr Ala Glu Ala Met Val Arg Ser Arg Glu Glu Asn
        435                 440                 445

Glu Phe Thr Asp Trp Phe Ser Leu Trp Gly Pro Trp His Ala Val Leu
                450                 455                 460

Lys Arg Thr Glu Ala Asp Arg Trp Ala Gln Ala Glu Glu Gln Lys Tyr
465                 470                 475                 480

Glu Met Leu Glu Asn Glu Tyr Pro Gln Arg Val Ala Asp Arg Leu Lys
                485                 490                 495

Ala Ser Gly Leu Ser Gly Asp Asp Ala Glu Arg Glu Ala Gly Ala
            500                 505                 510

Gln Val Met Arg Glu Thr Glu Gln Gln Ile Tyr Arg Gln Leu Thr Asp
        515                 520                 525

Glu Val Leu Ala Leu Arg Leu Phe Glu Asn Gly Ser Gln Leu His His
530                 535                 540

Ser
545
```